US012414994B2

(12) United States Patent
Hampson et al.

(10) Patent No.: US 12,414,994 B2
(45) Date of Patent: Sep. 16, 2025

(54) COMPOSITIONS COMPRISING LOPINAVIR AND TREATMENT OF CONDITIONS

(71) Applicant: DOUGLAS PHARMACEUTICALS LIMITED, Auckland (NZ)

(72) Inventors: Ian Hampson, Manchester Greater Manchester (GB); Lynne Hampson, Manchester Greater Manchester (GB); Fergus Cameron Binnie, Auckland (NZ); Peter Surman, Auckland (NZ)

(73) Assignee: DOUGLAS PHARMACEUTICALS LIMITED, Auckland (NZ)

( * ) Notice: Subject to any disclaimer, the term of this patent is extended or adjusted under 35 U.S.C. 154(b) by 709 days.

(21) Appl. No.: 17/610,962

(22) PCT Filed: May 20, 2020

(86) PCT No.: PCT/IB2020/054787
§ 371 (c)(1),
(2) Date: Nov. 12, 2021

(87) PCT Pub. No.: WO2020/234800
PCT Pub. Date: Nov. 26, 2020

(65) Prior Publication Data
US 2022/0257771 A1     Aug. 18, 2022

(30) Foreign Application Priority Data

May 23, 2019 (GB) ..................... 1907305

(51) Int. Cl.
| A61K 47/44 | (2017.01) |
| A61K 9/00 | (2006.01) |
| A61K 9/06 | (2006.01) |
| A61K 9/107 | (2006.01) |
| A61K 31/425 | (2006.01) |
| A61K 31/505 | (2006.01) |
| A61K 45/06 | (2006.01) |
| A61P 31/22 | (2006.01) |

(52) U.S. Cl.
CPC ............ *A61K 47/44* (2013.01); *A61K 9/0014* (2013.01); *A61K 9/0031* (2013.01); *A61K 9/0034* (2013.01); *A61K 9/06* (2013.01); *A61K 9/107* (2013.01); *A61K 31/425* (2013.01); *A61K 31/505* (2013.01); *A61K 45/06* (2013.01); *A61P 31/22* (2018.01); *A61K 2300/00* (2013.01)

(58) Field of Classification Search
CPC .... A61K 47/44; A61K 9/0014; A61K 9/0031; A61K 9/0034; A61K 9/06; A61K 45/06; A61P 31/22; A61P 31/12; A61P 17/00
See application file for complete search history.

(56) References Cited

U.S. PATENT DOCUMENTS

| 9,782,409 | B2 | 10/2017 | Hampson et al. |
| 10,251,884 | B2 | 4/2019 | Hampson et al. |
| 11,738,024 | B2 | 8/2023 | Hampson et al. |
| 12,083,120 | B2 | 9/2024 | Hampson et al. |
| 2002/0198160 | A1 | 12/2002 | Everitt et al. |
| 2003/0129208 | A1 | 7/2003 | Alberts et al. |
| 2005/0143404 | A1 | 6/2005 | Rosenberg et al. |
| 2010/0173861 | A1 | 7/2010 | Huang et al. |
| 2012/0219602 | A1 | 8/2012 | Flack et al. |
| 2016/0271132 | A1 | 9/2016 | Hampson et al. |
| 2018/0161328 | A1 | 6/2018 | Hampson et al. |
| 2021/0213015 | A1 | 7/2021 | Hampson et al. |
| 2021/0213016 | A1 | 7/2021 | Hampson et al. |
| 2023/0285287 | A1 | 9/2023 | Binnie et al. |
| 2024/0148729 | A1 | 5/2024 | Hampson et al. |
| 2025/0025464 | A1 | 1/2025 | Hampson et al. |

FOREIGN PATENT DOCUMENTS

| CN | 102083415 A | 1/2011 | |
| CN | 102614114 A | 8/2012 | |
| EP | 0366277 A2 | 5/1990 | |
| EP | 2613766 A2 | 7/2013 | |
| EP | 3603637 A1 | 2/2020 | |
| WO | 200152821 A1 | 7/2001 | |
| WO | 2004010937 A2 | 2/2004 | |
| WO | 2005007070 A2 | 1/2005 | |
| WO | 2005053694 A1 | 6/2005 | |
| WO | WO-2009129470 A2 * | 10/2009 | ........... A61K 9/0014 |
| WO | 2011128623 A2 | 10/2011 | |

(Continued)

OTHER PUBLICATIONS

Harmenburg et al Prevention of ulcerative lesions by episodic treatment of recurrent herpes labialis: "AI literature revew" Acta Derm Venerol 2010; 90: 122-130.

Piret, J et al "Antiviral resistance in herpes simplex virus and varicella zoster virus infections: Diagnosis and management" Current Opinion in Infectious Diseases. vol. 29 No. 6, 2016, (p. 654-662).

Katmusata et al "Antiviral efficacy of the helicase-primase inhibitor amenameir in murine models of severe herpesvirus infecetion" Biochem Pharm, vol. 158, 2018 (p. 201-206).

Kalu, et al., "Nelfinavir Inhibits Maturation and Export of Herpes Simplex Virus 1", Journal of virology vol. 88, No. 10, 2014 (p. 5455-5461).

(Continued)

*Primary Examiner* — Robert A Wax
*Assistant Examiner* — John Seungjai Kwon
(74) *Attorney, Agent, or Firm* — Linda B. Huber; Nixon Peabody LLP

(57) ABSTRACT

Provided herein are methods and compositions for treating and/or inhibiting the development or progression of conditions caused by, or associated with, Herpes Simplex Virus (HSV) infection. In particular, provided are compositions comprising lopinavir alone, or lopinavir and ritonavir, methods for their manufacture; and the use of said pharmaceutical compositions as a medicament. In particular, pharmaceutical compositions are provided for use in treating and/or inhibiting the progression of HSV related conditions.

19 Claims, 7 Drawing Sheets

(56) References Cited

FOREIGN PATENT DOCUMENTS

| WO | 2013034927 A1 | 3/2013 | |
| WO | WO-2015059485 A1 * | 4/2015 | ........... A61K 31/427 |
| WO | 2016123541 A2 | 8/2016 | |
| WO | WO-2019130341 A1 * | 7/2019 | ........... A61K 31/427 |
| WO | 2019224776 A1 | 11/2019 | |
| WO | 2019224777 A1 | 11/2019 | |
| WO | 2019224779 | 11/2019 | |
| WO | 2019224780 A1 | 11/2019 | |
| WO | 2020234800 A1 | 11/2020 | |
| WO | 2021105922 A1 | 6/2021 | |

OTHER PUBLICATIONS

Slyker, et al., "Acclerated Suppression of Primary Epstein-Barr Virus Infection in HIV-Infected Infants Initating Lopinvir/Ritonavir-Based Versus Nevirapine-Based Combination Antiretorviral Therapy" Clinical Infetion Diseases, vol. 58 No. 9, 2014 (p. 1333-13337).

Liu, et al, "Bowman-Birk inhibitor suppresses herpes simplex virus type 2 infection of human cervical epithelial cells" Viruses, vol. 10, 557, 2018 (p. 1-17).

Gantt, et al "Nelfinavir Impairs Glycosylation of Herpes Simples Virus 1 Envelope Proteins and Blocks Virus Maturation", Advances in Virology, 2015, (p. 1-9).

Gantt, et al, "The HIV Protease Inhibitor Nelfinavir Inhibits Kaposi's Sarcoma-Associated Herpesvirus Replication In Vitro" Antimicrobial Agents and Chemotherapy, vol. 55 No. 6, 2011 (p. 2696-2703).

International Search Report for PCT/IB2020/054787 mailed Nov. 13, 2020.

Exam Report for EP 19732473.4 dated Feb. 15, 2023, 3 pages.

Notice of Allowance for U.S. Appl. No. 17/055,067 dated May 6, 2024, 18 pages.

International Search Report and Written Opinion for PCT/GB2014/053169 dated Jan. 28, 2015, 11 pages.

International Search Report and Written Opinion for PCT/IB2019/054292 dated Sep. 17, 2019, 10 pages.

GB Search Report for GB1808563.9 dated Nov. 23, 2018, 2 pages.

International Search Report and Written Opinion for PCT/IB2019/054293 dated Sep. 5, 2019, 8 pages.

Anonymous, Kaletra Cream Attacks HPV, May Stop Cervical Cancer, 2006, retrieved from: http://www.natap.org/2006HIV/082506_02.htm on Jan. 19, 2015, 3 pages.

Batman et al., Lopinavir Up-Regulates Expression of the Antiviral Protein Ribonuclease L in Human Papillomavirus-Positive Cervical Carcinoma Cells, Antiviral Therapy, 2011, vol. 16, pp. 515-525.

Zehbe et al., Lopinavir Shows Greater Specificity than Zinc Finger Ejecting Compounds as a Potential Treatment for Human Papillomavirus-Related Lesions, Antiviral Research, 2011, vol. 91, pp. 161-166.

Mo et al., Characterization of resistant HIV variants generated by in vitro passage with lopinavir/ritonavir, Antiviral Research, 2003, vol. 59(3).

Hampson et al., A Single-Arm, Proof-of-Concept Trial of Lopimune (Lopinavir/Ritonavir) as a Treatment of HPV-Related Pre-Invasive Cervical Disease, PLOS One, 2016, vol. 11(1).

GlitterGalore, 2017, Lopinavir/ritonavir as a topical cream for HPV, CancerCompass, retrieved from: https://www.cancercompass./com/message-board/message/all,133989,0.htm.

Patel et al., Formulation of Niosomal Gel for Enhanced Transdermal Lopinavir Delivery and Its Comparative Evaluation with Ethosomal Gel, AAPS PharmSciTech, 2012, vol. 13(4), pp. 1502-1510.

EPO Exam Report for EP 20760530.4 dated Jan. 18, 2023, 7 pages.

UK Search Report for GB 1917252.7 dated May 22, 2020, 2 pages.

International Search Report and Written Opinion for PCT/IB2020/061183, dated Mar. 10, 2021, 10 pages.

Notice of Allowance for U.S. Appl. No. 17/055,048 dated Dec. 22, 2022, 7 pages.

Wagh et al., Solid Self-Emulsifying Drug Delivery System: Preparation Techniques and Dosage Forms, International Journal of Biopharmaceutics, 2014, vol. 5(2), pp. 101-108.

Reilly, The Sicence and Practice of Pharmacy, Remington pharmaceuticals science, 1995, 19th edition, pp. 1380 , 1397-1404.

* cited by examiner

A.

DMSO No Virus (-ve Cont.)

DMSO + HSV1

2µM Nelfinavir + HSV1

10µM Nelfinavir + HSV1

20µM 12:1 Lop/Rit + HSV1

B.

COMPOSITIONS COMPRISING LOPINAVIR AND TREATMENT OF CONDITIONS

CROSS-REFERENCE TO RELATED APPLICATIONS

This application is a National Phase of International Application No. PCT/IB2020/054787 filed May 20, 2020, which designated the U.S. and that International Application was published under PCT Article 21 (2) in English. This application also includes a claim of priority under 35 U.S.C. § 119 (a) and § 365 (b) to British Application No. GB 1907305.5 filed May 23, 2019, the entirety of which is hereby incorporated by reference.

Provided herein are methods and compositions for treating and/or inhibiting the development or progression of conditions caused by, or associated with, Herpes Simplex Virus (HSV) infection. In particular, provided are compositions comprising lopinavir alone, or lopinavir and ritonavir; methods for their manufacture; and the use of said pharmaceutical compositions as a medicament. In particular, pharmaceutical compositions are provided for use in treating and/or inhibiting the progression of HSV related conditions.

BACKGROUND

Human herpesviruses (HHV's) are large enveloped double-stranded DNA viruses that all have the characteristic of establishing life-long infections in humans. This is accomplished by their ability to exist in the host either as a symptom free latent infection, where the virus lies dormant or, following activation, as a lytic infection with the associated symptoms. It is notable that >90% of all humans are chronically infected with more than one HHV.

Herpes Simplex (HSV1&2 or HHV1&2) can cause disease in immunocompetent individuals and is a member of the alpha subfamily of herpesviruses which can target mucoepithelial cells. HSV1 & HSV2 can both cause cutaneous genital/anal and oro-labial/nasal cavity (cold sore) lesions although HSV2 is more commonly associated with the former and HSV1 the latter such that >80% of genital infections are caused by HSV2. Globally >500 million people have genital herpes infections which occur on the shaft or glans of the penis, scrotum and anus in men and on the vulva, vagina, cervix or perianal region in women although lesions can also occur on the buttocks and back of the thighs. Symptoms vary from individual to individual but are typically most severe on first time of infection and can last for 2-3 weeks. Approximately 50-80% of the world's population have oro-labial HSV infection which is the main cause of cold sores. HSV, and particularly HSV1, can also cause lesions on the fingers (Whitlows) and other areas of the skin.

Approximately 60% of HSV infected individuals will not get any noticeable symptoms and some will only ever get one cold sore in their lifetime whereas others can get them 4-5 times, or more, a year. In the USA 20-40% of the population will get recurrent labial HSV lesions and it is very significant that oro-labial cold sores and Whitlow's provide a very easy route for transmission of the virus to other individuals which can lead to rarer but much more serious HSV-related pathologies. For example, there are 50,000 cases per annum of HSV ocular Keratitis in the USA which is a major cause of blindness. HSV can also cause encephalitis in neonates which is a life-threatening condition.

The main topical treatment options for labial or skin HSV lesions have been the nucleoside analogues (NA's) acyclovir and penciclovir. Valaciclovir and famciclovir are other NA drugs used to counteract HSV, but their use is restricted to oral administration. However, NA drugs have limited efficacy. For instance, episodic topical application with 3-5% acyclovir or 1% penciclovir cream only improve healing times by approximately 10% (Harmenberg et al (2010) Acta Derm Venereol 2010; 90:122-130). Furthermore, there is a problem that acyclovir resistant strains are becoming increasingly more common, particularly in immune compromised individuals (Piret & Boivin (2016) Current Opinion in Infectious Diseases. 29(6):654-662).

Given the inadequacy of existing treatments for HSV, there is a need to develop new and improved treatments. A recent example of a drug being investigated is the helicase-primase inhibitor amenamevir (Katsumata et al. (2018) Biochem Pharm 158 p 201-206).

A recent advance in the treatment of cancers, particularly ones associated with viral infection, has been made by the inventors of the application in suit and is disclosed in WO2015/059485. WO2015/059485 describes the protease inhibitors, lopinavir and ritonavir (which have previously been used as orally ingested medicaments for the clinical management of retroviral infections such as HIV) as being clinically useful for topical administration to tissues to prevent or treat malignancies and in particular malignancies caused by human papilloma virus (HPV). The authors were particularly surprised to find that soft capsules of KALETRA® (which were marketed by Abbott/Abbvie for the treatment of HIV infections by oral administration) can be administered topically (e.g. inserted into the vagina for treatment of the cervix) for the prevention or treatment of cervical cancer.

KALETRA® (or its equivalent LOPIMUNE) is available for oral consumption as a solution comprising 80 mg lopinavir and 20 mg ritonavir per millilitre and was available as a soft capsule for oral administration that comprises 133.3 mg lopinavir and 33.3 mg ritonavir. In both cases the active pharmaceutical ingredients (APIs) are present in a ratio of 4:1 (lopinavir:ritonavir). The inventors have conducted further work (WO2019/224779) which indicates that altering the ratio of lopinavir:ritonoavir in a medicament has an impact on the efficacy of these protease inhibitors on cancer development.

The inventors also noted that Gantt et al. ((2011) Antimicrobial Agents and Chemotherapy Vol 55(6) p 2696-2'703) tested a number of anti-retroviral drugs to examine whether or not they influenced herpesvirus replication. Table 1 of the Gantt et al. paper illustrates that they found most of the drugs tested were ineffective for inhibiting herpesvirus. In fact, nelfinavir, was the only drug (other than gancylcovir which was a positive control) reported to have an inhibitory effect on viruses. It was particularly interesting to note that Gantt et al. found lopinvir and ritonavir, which one might assume would have as similar mode of action to nelfinavir, were ineffective. This paper appears to have been the inspiration for the authors (Gantt et al. ((2015) Advances in Virology Article ID 687162)) to further examine the effect of nelfinavir (but not lopinavir or ritonavir which they had presumably discounted) on the maturation and export of HSV1.

The inventors surprising observations (in connection with altering the ratio of lopinavir:ritonavir for cancer therapy) inspired the inventors to investigate the effects of different ratios of lopinavir and ritonavir on HSV infection and thereby examine if the state of the art (as discussed above), which suggests that lopinavir and ritonavir are poor choices for addressing HSV infection, is correct.

SUMMARY

Disclosed herein are compositions comprising lopinavir alone or in combination with ritonavir for use as a medicament for treating and/or inhibiting the development or progression of conditions caused by, or associated with, Herpes Simplex Virus (HSV).

Pharmaceutical compositions formulated for topical application comprising a therapeutically effective amount of lopinavir or a therapeutically effective amount lopinavir and ritonavir in a pharmaceutically acceptable vehicle are also provided.

In a preferred embodiment, compositions comprise a therapeutically effective amount of lopinavir in a pharmaceutically acceptable vehicle. Certain lopinavir only compositions have been found to provide particular benefits in respect to chemical stability and performance.

In another embodiment compositions comprise a therapeutically effective amount of lopinavir and ritonavir in a pharmaceutically acceptable vehicle wherein the weight (w/w) ratio of lopinavir:ritonavir is between 9:1 and 18:1. Preferably the weight (w/w) ratio of lopinavir:ritonavir is about 12:1.

Also disclosed are methods of treating a patient to treat and/or inhibit the development or progression of conditions caused by, or associated with, Herpes Simplex Virus (HSV) comprising administering to said patient a therapeutically effective dose of the disclosed pharmaceutical compositions.

BRIEF DESCRIPTION OF THE DRAWINGS

The summary, as well as the following detailed description, is further understood when read in conjunction with the appended drawings. For the purpose of illustrating the disclosed compositions and methods, there are shown in the drawings exemplary embodiments of the compositions and methods; however, the compositions and methods are not limited to the specific embodiments disclosed. In the drawings:

FIG. 1A shows phase contrast images of the effects of HSV2 infection on the morphology of N-Tert keratinocytes exposed to either DMSO control or 20 µM lopinavir for 48 hours; FIG. 1B shows images of anti-HSV antibody immunostaining of the cells of FIG. 1A; and FIG. 1C shows quantitative analysis of the percentage of HSV2 positive cells detected by immune staining.

FIG. 2A shows representative images of anti-HSV immune-stained HSV2 infected N-Tert keratinocytes treated with the indicated concentrations and mixtures of the different APIs; and FIG. 2B shows the effect of 2 µM, 5 µM and 10 µM nelfinavir and 20 µM 12:1 Lop/Rit against HSV2 replication.

FIG. 4A illustrates representative images of anti-HSV1 immune-stained HSV1 infected N-Tert keratinocytes treated with the indicated concentrations and mixtures of the different APIs; and FIG. 4B shows the effect of 2 µM and 10 µM nelfinavir and 20 µM 12:1 w/w Lop/Rit against HSV1 replication.

FIG. 5A illustrates representative images of anti-HSV immuno-stained HSV1 infected N-Tert keratinocytes treated with the indicated concentrations and mixtures of the different APIs; and FIG. 5B illustrates the effects of 2 µM and 10 µM nelfinavir; 20 µM 4:1 w/w Lop/Rit; 20 µM 12:1 w/w Lop/Rit; and 20 µM Lopinavir against HSV1 replication following a change to the protocols followed for FIG. 5A (two hour reduction in overnight pre-treatment virus incubation time).

FIG. 6A illustrates representative images of anti-HSV immuno-stained acyclovir resistant (Ac Res) HSV2 infected N-Tert keratinocytes treated with indicated concentrations of different APIs; and FIG. 6B illustrates the effects of 5 µM Acyclovir; 10 µM and 20 µM Lopinavir on Ac Res HSV2 replication.

DETAILED DESCRIPTION

Figure 1:
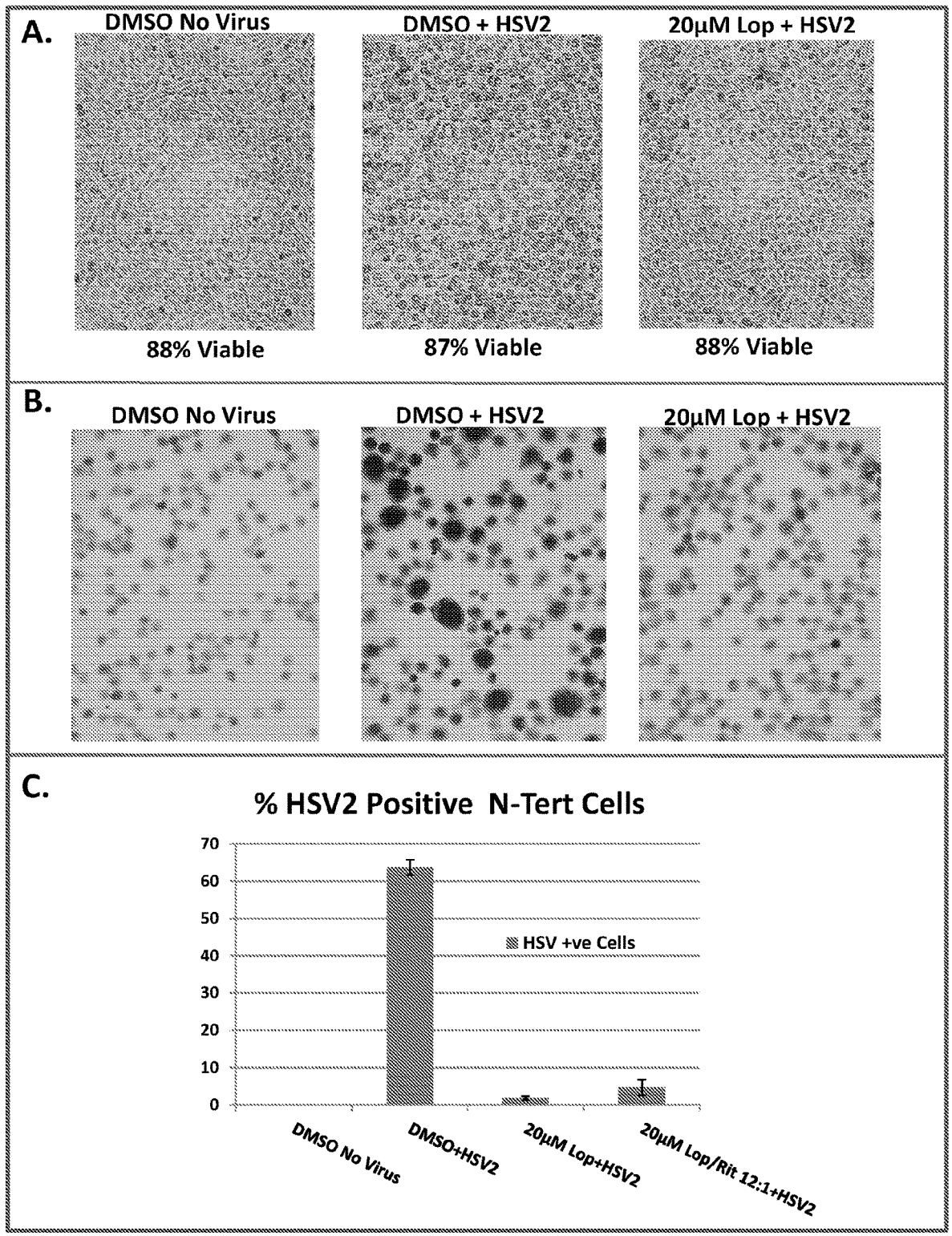
FIG. 1.

The disclosed compositions, uses thereof and methods may be understood more readily by reference to the following detailed description taken in connection with the accompanying figures, which form a part of this disclosure. It is to be understood that the disclosed compositions and methods are not limited to the specific compositions and methods described and/or shown herein, and that the terminology used herein is for the purpose of describing particular embodiments by way of example only and is not intended to be limiting of the claimed compositions and methods.

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

When values are expressed as approximations, by use of the antecedent "about," it will be understood that the particular value forms another embodiment.

It is to be appreciated that certain features of the disclosed compositions and methods which are, for clarity, described herein in the context of separate embodiments, may also be provided in combination in a single embodiment. Conversely, various features of the disclosed compositions and methods that are, for brevity, described in the context of a single embodiment, may also be provided separately or in any sub-combination.

As used herein, the singular forms "a," "an," and "the" include the plural.

The following abbreviations are used herein: Herpes Simplex Virus (HSV); Human herpesviruses (HHV); acyclovir resistant HSV (AR HSV); Active Pharmaceutical Ingredient (API); and human papilloma virus (HPV).

The term "about" when used in reference to numerical ranges, cut-offs, or specific values is used to indicate that the recited values may vary by up to as much as 10% from the listed value. As many of the numerical values used herein are experimentally determined, it should be understood by those skilled in the art that such determinations can, and often times will, vary among different experiments. The values used herein should not be considered unduly limiting by virtue of this inherent variation. Thus, the term "about" is used to encompass variations of ±10% or less, variations of ±5% or less, variations of ±1% or less, variations of ±0.5% or less, or variations of ±0.1% or less from the specified value.

As used herein, "treating" and like terms refer to reducing the severity and/or frequency of HSV induced symptoms, eliminating HSV induced symptoms and/or the underlying cause of said symptoms, reducing the frequency or likelihood of HSV induced symptoms and/or their underlying cause, delaying, preventing and/or slowing the progression of HSV induced conditions (e.g. cold sores), and improving or remediating damage caused, directly or indirectly, by HSV infections.

As used herein, the phrase "therapeutically effective dose" refers to an amount of a composition comprising lopinavir, or lopinavir and ritonavir, as described herein, effective to achieve a particular biological or therapeutic result such as, but not limited to, biological or therapeutic results disclosed, described, or exemplified herein. The therapeutically effective dose may vary according to factors such as the disease state, age, sex, and weight of the individual, and the ability of the composition to cause a desired response in a subject. Such results include, but are not limited to, the reduction, remission, and/or regression of conditions caused by, or associated with, HSV or prevention of the development of conditions caused by, or associated with, HSV, as determined by any means suitable in the art.

As used here, "subject" includes a vertebrate, mammal, domestic animal or preferably a human being.

The "pharmaceutically acceptable vehicle" may be any physiological vehicle known to those of ordinary skill in the art useful in formulating pharmaceutical compositions.

Disclosed herein are compositions comprising lopinavir or lopinavir and ritonavir for use as a medicament for treating and/or inhibiting the development or progression of conditions caused by, or associated with, Herpes Simplex Virus (HSV) and in particular HSV1 or HSV2.

Contrary to what was known from the prior art, lopinavir alone or lopinavir with ritonavir, are effective for addressing HSV infection. Furthermore, as described below, lopinavir +/−ritonavir, is surprisingly better than nelfinavir because compositions according to the invention not only have improved efficacy but also cause less toxicity to uninfected host cells. Furthermore compositions comprising lopinavir (+/−ritonavir) are particularly useful for treating conditions caused by, or associated with, acyclovir resistant HSV.

The compositions according to the first aspect of the invention are useful for treating and/or inhibiting the development or progression of conditions caused by, or associated with, HSV and particularly useful for preventing the development of cold sores, whitlows, genital or anal herpes in addition to other HSV related conditions, including ocular HSV related conditions, such as ocular keratitis.

It is preferred that the compositions are formulated in a medicament that is suitable for topical application. In a most preferred embodiment, the medicament is formulated such that it is suitable for topical delivery of the active ingredients to the epidermis (e.g. as a gel, cream, paste, non-aqueous emulsion, lip-balm (including a lip-balm contained in a lipstick-style tube), stick or ointment) for preventing the development of, or treating and/or inhibiting the development or progression of conditions caused by, or associated with, HSV.

Lopinavir (CAS #192725-17-0) is a protease inhibitor chemically designated as [1S-[1R*(R*), 3R*, 4R*]]-N-[4-[(2,6-dimethylphenoxy0acetyl]amino]-3-hydroxy-5-phenyl-1-(phenylmethyl)pentyl]tetrahydro-alpha-(1-methylethyl)-2-oxo-1(2H)-pyrimidineacetamide. It has the molecular formula $C_{37}H_{48}N_4O_5$ and a molecular weight of 628.80.

Ritonavir (CAS #155214-67-5) is a protease inhibitor chemically designated as 10-Hydroxy-2-methyl-5-(1-methylethyl)-1-[2-(1-methylethyl)-4-thiazolyl]-3,6-dioxo-8,11bis(phenylmethyl)-2,4,7,12-tetraazatridecan-13-oic acid, 5-thiazolylmethylester, [5S-(5R*,8R*,10R8,11R*)]. It has the molecular formula $C_{37}H_{48}N_6O_5S_2$ and a molecular weight of 720.95.

Compositions Comprising Lopinavir

WO2015/059485 discloses that lopinvair alone is not as effective as compositions comprising lopinavir and ritonavir in the treatment of cervical cancer and other HPV related conditions. Furthermore Gantt et al. (supra) reported that nelfinavir, but not lopinavir and ritonavir, was able to inhibit herpesvirus. In view of the prior art it was with great surprise that the inventor found lopinavir alone had efficacy for inhibiting the growth and/or eliminating HSV infection. The examples illustrate that 20 µM lopinavir was significantly better at reducing infection than concentrations of nelfinavir up to 10 µM.

Figure 3:
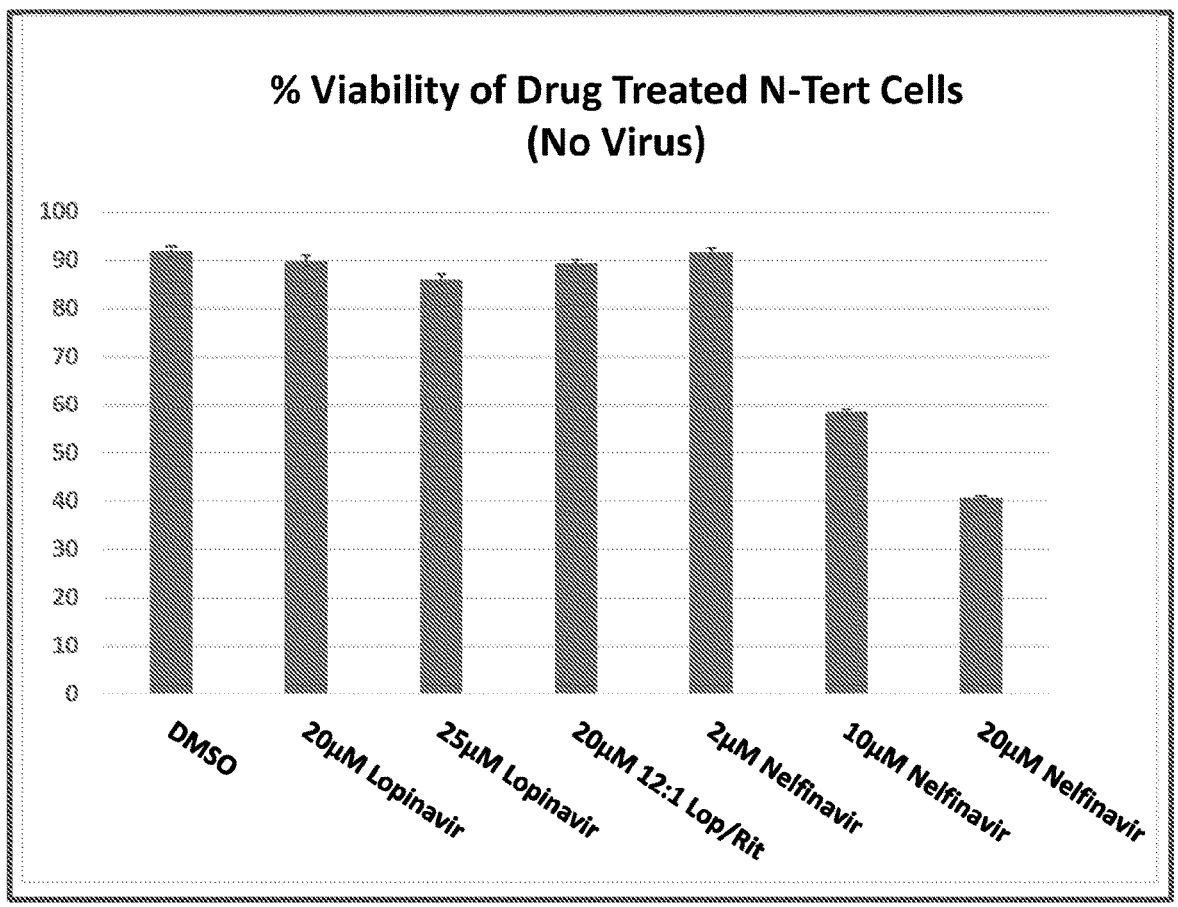
FIG. 3: shows Via-1 cassette viability assays on uninfected N-Tert keratinocytes treated for 48 hours with the indicated concentrations and mixtures of APIs shown.
Figure 4:
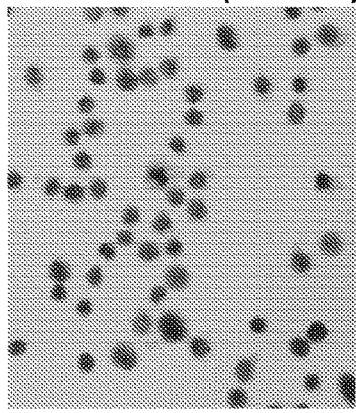
FIG. 4.
Figure 4:
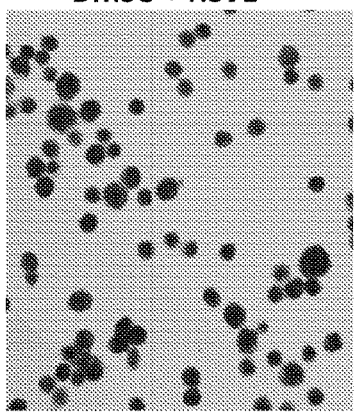
Figure 4:
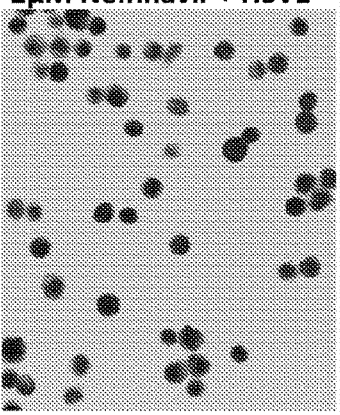
Figure 4:
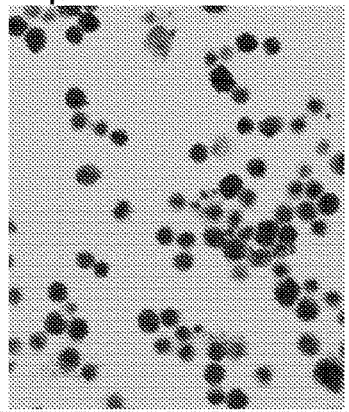
Figure 4:
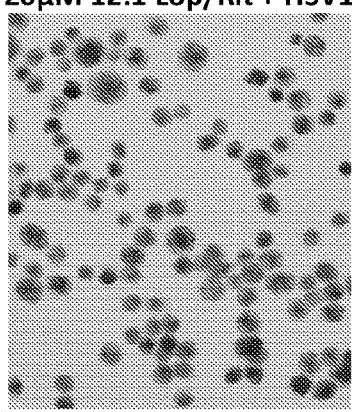
Figure 4:
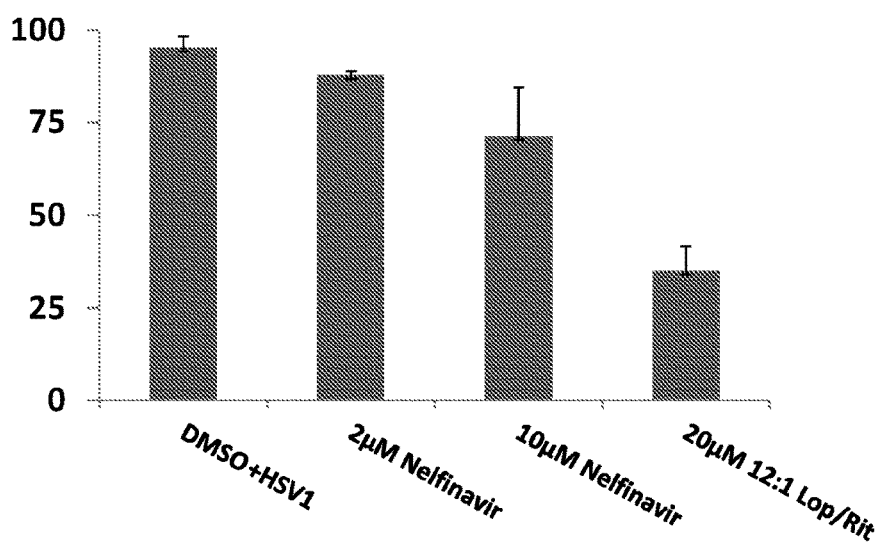

It is interesting that Gantt et al. (supra) only reported testing nelfinavir up to 10 µM. The inventors believe Gantt et al did not report above this concentration because higher concentrations would have been highly toxic to the cell line infected with the virus. The inventors found at concentrations above 2 µM, that nelfinavir had significant toxic effects on eukaryotic cells (e.g. see FIG. 3). This has led the inventors to believe that nelfinavir has a very narrow therapeutic window. For instance they found that 2 µM nelfinavir only had modest effects (e.g. see FIG. 4B), but then became unacceptably toxic at 10 µM nelfinavir and above (FIG. 3). In contrast to nelfinavir, and to the inventors surprise, lopinavir was particularly effective (and more so than nelfinavir) at clearing virus and, importantly, did so without having any significant toxic effects against an uninfected eukaryotic host cell (see the examples).

In a preferred embodiment lopinavir is used such that a concentration of lopinavir is achieved at the target site (e.g. a cold sore lesion) will be between 0.1 µM and 100 µM. Preferably the concentration of lopinavir will be between 0.5 µM and 50 µM and more preferably between 1.0 µM and 30 µM. Examples of preferred concentrations include between 20 µM and 25 µM lopinavir. It will be appreciated that compositions according to the invention which are applied topically to a lesion (ointments, creams and the like) may comprise lopinavir at these concentrations.

In another preferred embodiment lopinavir is used to treat conditions caused by acyclovir resistant HSV. In this case lopinavir may be used in the same concentrations contemplated in the preceding paragraph.

Compositions Comprising Lopinavir and Ritonavir

The prior art suggests that combinations of lopinavir and ritonavir will not be effective against HSV (Gantt et al. supra). However surprisingly the inventors have found that compositions comprising lopinavir and ritonavir are effective for inhibiting HSV. For instance, FIG. 5B illustrates that 4:1 Lopinavir:ritonavir (i.e. the ratio found in KALETRA®) is effective against HSV without being toxic to the host cell. Furthermore it is more effective than concentrations of nelfinavir which are within its therapeutic window.

Based on the inventors' unpublished observations when researching the efficacy of lopinavir and ritonavir for treating cancer, they varied the ratio of the APIs and found that certain molar ratios of lopinavir:ritonavir are even more useful for treating and/or inhibiting the development or progression of conditions caused by, or associated with, HSV. FIG. 5b illustrates that a ratio of 12:1 was significantly better than nelfinavir and also even better than 4:1 lopinavir:ritonavir. The inventors found combinations of lopinavir and ritonavir are most effective if the APIs are in a molar ratio range of 10:1-18:1. The range may be 10.5:1-18:1. Preferably the range is 10.5:1-17:1, more preferably 11.0:1-16.0:1 and even more preferably 11.5:1-14:1 The range may be a molar ratio of about 11:0:1, about 11.5:1; about 12:1; about 12.5:1; about 13:1; about 13.5:1; about 13.75:1; about 14:0:1; or about 14:5:1. In a preferred embodiment the molar ratio of lopinavir:ritonavir is about 12:1. In another preferred embodiment the molar ratio of lopinavir:ritonavir is about 13.8:1.

It will be appreciated that lopinavir has a molecular weight of 628.8 daltons and ritonavir has a molecular weight of 720.95 daltons. Accordingly molar ratios and w/w ratios will not be the same and a factor of 0.872 should be applied when converting molar ratios to w/w. Accordingly the inventors have found that w/w ratios of lopinavir:ritonavir for treating and/or inhibiting the development or progression of conditions caused by, or associated with, HSV may be in the weight ratio range 9:1-18:1. The range may be 9.5:1-18:1. For instance the range may be 9.5:1-16:1 or 10.0:1-16:1. Preferably the range is 10.0:1-15.0:1, more preferably 10.25:1-14.5:1 and most preferably 10.5:1-13.0:1. The range may be a w/w ratio of about 10.25:1; about 10.5:1; about 10.75:1; about 11:1; about 11.25:1; about 11.5:1; about 11.75:1; about 12.0:1; about 12.25:1; about 12.5:1; about 12.75: about 13.0:1; about 13.25:1; about 13.5:1; about 13.75:1; about 14.0:1 or about 14:25:1. In a preferred embodiment the w/w ratio of lopinavir:ritonavir is about 10.5:1. In a most preferred embodiment the w/w ratio of lopinavir:ritonavir is about 12:1.

In a preferred embodiment a sufficient amount of lopinavir and ritonavir is used such that a concentration of the combined APIs at the target site (e.g. a cold sore lesion) will be between 0.1 µM and 100 µM. Preferably the concentration of combined APIs will be between 0.5 µM and 50 µM and more preferably between 1.0 µM and 30 µM. Examples of preferred concentrations include be between 20 µM and 25 µM lopinavir and ritonavir. It will be appreciated that compositions according to the invention which are applied topically to a lesion (ointments, creams and the like) may comprise lopinavir and ritonavir at these concentrations.

Uses of Compositions According to the Invention

The compositions according to the first aspect of the invention are useful in the treatment of conditions such as cold sores, whitlows, genital or anal herpes or ocular HSV related conditions, such as ocular keratitis.

The compositions according to the first aspect of the invention are also useful in preventing the development of HSV-related conditions. Accordingly, normal subjects (i.e. subjects with no detectable disease or condition) and particularly subjects prone to such conditions (e.g. cold sores) may be treated by topical administration of compositions according to the invention with a view to preventing the development of such conditions.

Furthermore, as illustrated in the Examples, the inventors have found that compositions according to the invention are particularly useful for preventing the reoccurrence of conditions caused by, or associated with, HSV. The inventors were most surprised to find that a single course of treatment (see below) had long term efficacy for preventing the reoccurrence of conditions, or at least reducing the number of occasions when there is reoccurrence.

The compositions may be given to subjects with a genetic disposition to developing HSV-related conditions or even those facing environmental risk (e.g. health workers).

The compositions may be used for treating and/or inhibiting the development or progression of conditions caused by, or associated with, HSV as a monotherapy (i.e. use of lopinavir alone; or lopinavir and ritonavir alone) or in combination with other compounds or treatments used to treat HSV related conditions.

It is most preferred that the compositions are used to treat humans. However, it will be appreciated that the compositions may also have some veterinary use.

Pharmaceutical Compositions

Compositions according to the invention are formulated as a medicament that is suitable for topical application and may in particular be formulated for administration to the skin, including mucosal surfaces.

Suitable formulations include, but are not limited to, a gel, cream, paste, ointment, a lotion, a non-aqueous emulsion, a solid or semi-solid stick composition, or a lip-balm (including a lip-balm contained in a lipstick-style tube). In some aspects, the pharmaceutical composition can be formulated as a gel. In some aspects, the pharmaceutical composition can be formulated as a cream. In some aspects, the pharmaceutical composition can be formulated as a paste. In some aspects, the pharmaceutical composition can be formulated as an ointment. In some aspects, the pharmaceutical composition can be formulated as a lotion. In some aspects, the pharmaceutical composition can be formulated as a solid or semi-solid stick composition. In some aspects, the pharmaceutical composition can be formulated as a lip-balm (including a lip-balm contained in a lipstick-style tube). In some aspects, the pharmaceutical composition can be formulated as a non-aqueous emulsion.

In preferred embodiments, the composition is formulated such that it is suitable for topical delivery of the APIs to the skin (e.g. as an ointment, gel, paste, lotion, non-aqueous emulsion, a solid or semi-solid stick composition, a lip-balm (including a lip-balm contained in a lipstick-style tube) or a cream).

When used to treat (or prevent the development of) cold sores, whitlows or genital or anal herpes the compositions can be formulated as gels, lotions, paste, creams, non-aqueous emulsions, solid or semi-solid stick compositions, lip-balms (including lip-balms contained in lipstick-style tubes) or ointments that may be applied directly to the target site by techniques known to the art.

Preferred compositions for use according to the invention are formulated for use as oral-labial, nasal cavity, ocular, skin or mucosal treatments and may comprise lopinavir alone. Other preferred compositions for use according to the invention are formulated for use as oral-labial, nasal cavity, ocular, skin or mucosal treatments comprising lopinavir and ritonavir.

In one embodiment, the pharmaceutically acceptable vehicle can be a liquid and the composition can be a solution. In another embodiment, the vehicle can be a gel and the composition can be a gel for applying to the skin. In a further embodiment, the vehicle can be an emulsion (or other pharmaceutically acceptable base) and the composition can be a skin cream. In a further embodiment, the vehicle can be smooth and oily and the composition can be an ointment for application to the skin, oral labia, nasal cavity, peri-anal area or genitals. In a further embodiment, the vehicle can be a waxy solid or semi-solid and the composition can be a stick composition or a lip-balm contained in a lipstick-style tube suitable for application to the skin, oral labia or nasal cavity.

Liquid vehicles may be used in preparing gels, lotions, creams, solutions, suspensions and emulsions. The active ingredient can be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilizers, emulsifiers, buffers, preservatives, suspending agents, thickening agents, colours, viscosity regulators, stabilizers or osmo-regulators. Suitable examples of liquid vehicles include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). The vehicle can also be an oily ester such as ethyl oleate and isopropyl myristate. The liquid vehicle for pressurized compositions can be halogenated hydrocarbon or other pharmaceutically acceptable propellant.

The more flowable semi-solid vehicles can be packaged into applicators, syringes, tubes for dispensing. Less-flowable, stiff semi-solid/solid vehicles can be packaged into stick form for direct contact transfer to the affected site.

In one embodiment the composition typically may use polyethylene glycol as a main vehicle for lopinavir; or lopinavir and ritonavir. The balance of the vehicle may be made up of, for example, Oleic acid, PEG 35, castor oil, purified water, gelatin, sorbitol special polyol, or any combination thereof. Lopinavir and ritonavir are virtually insoluble in water and it is preferred that such organic bases (or equivalents thereof) are used.

Preferred pharmaceutical compositions are creams, lotions or ointments and comprise vehicles most suited for application to the skin. Some of these formats have water present within the composition. However topical compositions which contain water are not always ideal for use with an API which is prone to degradation by hydrolysis because this may result in a short shelf life of the pharmaceutical product and/or the requirement to store the composition in certain conditions in order to minimize degradation of the active API. Lopinavir and ritonavir are examples of APIs which can be prone to degradation. Therefore, preferred compositions may comprise non-aqueous vehicles. Such vehicles are typically smooth oily compositions and typically contain a significant proportion (w/w) of pharmaceutically acceptable oils or fats (e.g. oleic acid). Such vehicles can contain other suitable pharmaceutical additives such as solubilizers, emulsifiers, buffers, preservatives, suspending agents, thickening agents, colours, viscosity regulators, stabilizers or osmo-regulators.

It will be appreciated that the amount of lopinavir; or lopinavir and ritonavir in compositions according to the invention will depend up the exact components and in particular the vehicle for the composition.

In one embodiment lopinavir is the sole API in the composition. By way of example only, suitable amounts of lopinavir in such a composition may be from about 0.1-30% w/w. In some embodiments, the amount of lopinavir in the composition can be from about 1.0-25% w/w. In some embodiments, the amount of lopinavir in the composition can be from 2.0-20% w/w. In some embodiments, the amount of lopinavir in the composition can be from 6.0 to 20% w/w. In some embodiments, the amount of lopinavir in the composition can be from 8 to 15% w/w. For instance, an ointment may comprise about 5%, 6%, 10% or 12% (w/w) lopinavir.

In another embodiment lopinavir and ritonavir are in the composition. By way of example only, suitable amounts of lopinavir in such a composition comprising may be from about 0.1-30% w/w. In some embodiments, the amount of lopinavir in the composition can be from about 1.0-25% w/w. In some embodiments, the amount of lopinavir in the composition can be from 2.0-20% w/w. For instance, and ointment may comprise about 5%, 6%, 10% or 12% (w/w) lopinavir. Suitable amounts of ritonavir in such compositions may be from about 0.01-3% w/w. In some embodiments, the amount of ritonavir in the composition can be from about 0.1-2.5% w/w. In some embodiments, the amount of ritonavir in the composition can be from 0.15-1.5% w/w. For instance, an ointment may comprise about 0.4775%, 0.5%, 0.625% or 0.955% (w/w) ritonavir. A preferred composition may comprise about 8 to about 14% by weight of lopinavir and about 0.75 to about 1.4% by weight of ritonavir. For example, the composition may comprise by weight 10% lopinavir and 0.955% ritonavir or the composition may comprise by weight 12% lopinavir and 1% ritonavir. Another preferred composition may comprise about 4 to about 7% by weight of lopinavir and about 0.375 to about 0.75% by weight of ritonavir. For example, the composition may comprise by weight 5% lopinavir and 0.4775% ritonavir or the composition may comprise by weight 6% weight lopinavir and 0.5% ritonavir.

Preferred Compositions

A preferred composition for use according to the invention is a pharmaceutical composition comprising:
a. an unsaturated free fatty acid;
b. a stiffening agent; and
c. lopinavir alone; or lopinavir and ritonavir in a weight ratio of between 9:1 and 18:1;
wherein the unsaturated free fatty acid is present at a level of at least 20% by weight of the total pharmaceutical composition weight and wherein the pharmaceutical composition is a solid or semi-solid at room temperature.

When the two APIs are used, the weight ratio of lopinavir: ritonavir is preferably between 10:5:1 and 13.5:1 and most preferably about 12.0:1 (w/w).

A semi-solid is any material that can be present in a stationary material state until an external stress is applied resulting in flow of the material. The physical properties of a semi-solid are a mixture of a solid and liquid. It will be apparent to the skilled person that the pharmaceutical composition is in a form of a semi-solid, for example by testing the pharmaceutical composition using a rheometer. From rheometric testing of the pharmaceutical composition the yield stress, the storage modulus, the loss modulus and tan δ can be determined. The yield stress is a direct measure for the initiation of material flow (solid state to fluid state) in response to an applied stress. The storage modulus is a direct measure of a fluid's solid-like behaviour. The loss modulus is a direct measure of a fluid's fluid-like behaviour. Tan δ is the ratio of the loss modulus to the storage modulus and is a unitless measure. A tan δ value of <1 defines a material as largely solid like, while a tan δ value >1 defines a material as predominantly fluid-like.

In one embodiment, the pharmaceutical composition has a tan δ value of between about 0.5 and about 1.5 at 37° C., such as about 0.8 and about 1.2.

Conventional compositions often employ vegetable oils and/or polysorbates as agents to thicken the composition. It has been advantageously established that an unsaturated free fatty acid and a stiffening agent can be used to prepare a pharmaceutical composition which is a semi-solid at room temperature that can be present in a stationary material state until an external stress is applied resulting in flow of the material. Such an external stress can be the application of the composition to a target tissue (i.e. the skin) and the inventors have found that such compositions are particularly effective for delivering lopinavir and ritonavir to the skin.

Advantageously, the pharmaceutical composition only comprises fats in the form of free fatty acids (unsaturated free fatty acid and/or saturated free fatty acid), for example all fatty acids present in the composition are in the form of a free fatty acid. This allows the pharmaceutical composition to be manufactured at room temperature which is advantageous when the APIs are prone to degradation, and wherein the rate and/or extent of degradation is increased when the API is exposed to heat.

Unsaturated Free Fatty Acids

The unsaturated free fatty acid may be selected from oleic acid, linoleic acid, alpha-linoleic acid, palmitoleic acid, gondoic acid, and ricinoleic acid. The unsaturated free fatty acid is preferably oleic acid.

In one embodiment, of the total unsaturated fatty acid (bound and free form unsaturated fatty acid) present within the composition, at least 90% by weight is in the free form, (i.e. not esterified or bound to other components such as glycerol) At least 95% by weight may be in the free form, at least 98% by weight may be in the free form, at least 99% by weight may be in the free form, or at least 99.5% by weight may be in the free form. The skilled person would be aware of methods used to determine the free fatty acid content versus the total fatty acid content. For example, the free fatty acid content can be measured by reacting the free fatty acid with a chromogenous compound, thus changing the frequency that the chromogeous compound absorbs electromagnetic radiation. Thus, the concentration of the chromogenous compound reacted can be determined by monitoring the chromogenous compound using a suitable wavelength which in turn can be used to determine the free fatty acid content in the sample.

It is to be understood that free fatty acids products that are commercially available may contain small amounts of other free fatty acids. For example, oleic acid typically contains 7-12% saturated free fatty acids, such as stearic and palmitic acid, together with other unsaturated free fatty acids, such as linoleic acid (Handbook of Pharmaceutical Excipients, $2^{nd}$ Edition, see entry for Oleic acid). The terms saturated free fatty acid or unsaturated free fatty acid are to be understood as meaning the saturated free fatty acid or the unsaturated free fatty acid are of Pharmacopeia grade, such as the US Pharmacopeia and/or the British Pharmacopeia, and that the saturated free fatty acid or unsaturated free fatty acid may contain small amounts of other free fatty acids.

In one embodiment, the unsaturated free fatty acid is not in the form of a triglyceride or polysorbate.

The total fatty acid (unsaturated and saturated fatty acids in the bound and free form) present within the composition may be at least 90% by weight, such as at least 95% by weight such as at least 98% by weight, such as at least 99% by weight, or such as at least 99.5% by weight, in the free form, i.e., not esterified or bound to other components such as glycerol.

Stiffening Agents

The stiffening agent is an excipient used to stiffen the composition so that the composition is a solid or semi-solid at room temperature. Conveniently, the stiffening agent is a saturated free fatty acid, such as a $C_{10}$-$C_{38}$ saturated free fatty acid, such as a $C_{16}$-$C_{22}$ free fatty acid. A saturated free fatty acid is a free fatty acid (i.e., the fatty acid is not bound to another molecule, such as glycerol) wherein there are no double bonds between the carbon atoms in the fatty acid. In one embodiment, the stiffening agent is selected from capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid and octatriacontanoic acid. The stiffening agent is preferably stearic acid.

In one embodiment, of the total saturated fatty acid (bound and free form fatty acid) present within the composition, at least 90% by weight, such as at least 95% by weight such as at least 98% by weight, such as at least 99% by weight, or such as at least 99.5% by weight, is in the free form, i.e., not esterified or bound to other components such as glycerol. The skilled person would be aware of methods used to determine the free fatty acid content versus the total fatty acid content. For example, the free fatty acid content can be measured by reacting the free fatty acid with a chromogenous compound, thus changing the frequency that the chromogeous compound absorbs electromagnetic radiation. Thus, the concentration of the chromogenous compound reacted can be determined by monitoring the chromogenous compound using a suitable wavelength which in turn can be used to determine the free fatty acid content in the sample.

In one embodiment, the saturated free fatty acid is not in the form of a triglyceride or polysorbate.

The unsaturated free fatty acid is preferably oleic acid and the stiffening agent is preferably stearic acid.

Other Components of the Compositions

Compositions according to the invention may optionally include a muco-adhesive agent and other excipients as described below.

The compositions may comprise a mucoadhesive agent. The muco-adhesive may be a non-ionic polymer or an ionic polymer. In one embodiment, the non-ionic polymer is a cellulose ether. In one embodiment, the cellulose ether is selected from methyl cellulose, ethylcellulose and hydroxypropylmethylcellulose.

In a preferred embodiment, the muco-adhesive is hydroxypropylmethylcellulose. In one embodiment, the hydroxypropylmethylcellulose has a degree of methoxy substitution of between 19 and 24% by weight and a degree of hydroxypropyl substitution of between 4 and 12% by weight.

In another embodiment, the ionic polymer is sodium polyacrylate.

Optionally, additional excipients may be included in the compositions. Suitable examples of additional excipients, which may be included in the composition include thickeners, blending agents and antioxidants.

In one embodiment, the composition further comprises a thickener. A thickener is an excipient which when added to a mixture increases the viscosity of the mixture and confers the anhydrous composition with greater physical stability and/or control during delivery of the active pharmaceutical ingredient to the site of application. In one embodiment, the thickener is selected from mono di glyceride, ceresin wax, and hydrogenated vegetable oil.

In one embodiment, the composition further comprises a thickener. A blending agent is an agent which promotes uniformity within the pharmaceutical composition, for example it promotes uniformity for organoleptic attributes within the pharmaceutical composition. In one embodiment, the blending agent is selected from polyoxy 100 stearate and glycerol monooeleate.

In one embodiment, the pharmaceutical composition comprises an antioxidant. In one embodiment, the antioxidant is butylated hydroxytoluene or butylated hydroxyanisole. In one embodiment, the antioxidant is present in the pharmaceutical composition at about 0.05 to about 0.5% by weight of the total pharmaceutical composition by weight, such as about 0.05 to about 0.15% by weight, such as about 0.1 to about 0.3% by weight, such as about 0.2% by weight.

In one embodiment, there is provided a composition for topical application to the skin comprising:
  a. lopinavir and optionally ritonavir;
  b. oleic acid; and
  c. stearic acid.

Such a composition may further comprise one, more or all of an ingredient selected from mono di glyceride, ceresin wax, and hydrogenated vegetable oil.

In one embodiment, there is provided a composition for topical application comprising:
  a. lopinavir and optionally ritonavir;
  b. hydroxypropylmethylcellulose;
  c. oleic acid;
  d. stearic acid; and
  e. butylated hydroxytoluene In one embodiment, the composition contains lopinavir alone and comprises:
  a. about 9 to about 11% by weight of lopinavir;
  b. about 0.5 to about 1.5% by weight of hydroxypropylmethylcellulose;
  c. about 55 to about 65% by weight of oleic acid;
  d. about 28 to about 32% by weight of stearic acid; and
  e. about 0.0.5 to about 0.5% by weight of butylated hydroxytoluene;
wherein all % are by weight based upon the total weight of the composition.

In another embodiment, the composition contains lopinavir alone and comprises:
  a. about 4 to about 6% by weight of lopinavir;
  b. about 0.5 to about 1.5% by weight of hydroxypropylmethylcellulose;
  c. about 55 to about 65% by weight of oleic acid;
  d. about 28 to about 32% by weight of stearic acid; and
  e. about 0.05 to about 0.5% by weight of butylated hydroxytoluene;
wherein all % are by weight based upon the total weight of the composition.

In another embodiment, the composition contains lopinavir and ritonavir and comprises
  a. about 1.2 to about 1.4% by weight of ritonavir;
  b. about 9 to about 11% by weight of lopinavir;
  c. about 0.5 to about 1.5% by weight of hydroxypropylmethylcellulose;
  d. about 55 to about 65% by weight of oleic acid;
  e. about 28 to about 32% by weight of stearic acid; and
  f. about 0.05 to about 0.5% by weight of butylated hydroxytoluene;
wherein all % are by weight based upon the total weight of the composition.

In another embodiment, the composition contains lopinavir and ritonavir and comprises:
  a. about 0.5 to about 0.7% by weight of ritonavir;
  b. about 4 to about 6% by weight of lopinavir;
  c. about 0.5 to about 1.5% by weight of hydroxypropylmethylcellulose;
  d. about 55 to about 65% by weight of oleic acid;
  e. about 28 to about 32% by weight of stearic acid; and
  f. about 0.05 to about 0.5% by weight of butylated hydroxytoluene;
wherein all % are by weight based upon the total weight of the composition.

A preferred composition comprises:
  a. lopinavir and optionally ritonavir;
  b. hydroxypropylmethylcellulose;
  c. oleic acid;
  d. stearic acid;
  e. butylated hydroxytoluene;
  f. mono diglyceride;
  g. ceresin wax;
  h. hydrogenated vegetable oil;
  i. polyoxyl 100 stearate; and
  j. glycerol monooleate;

In one embodiment, the composition contains lopinavir alone and comprises:
  a. about 9 to about 11% by weight of lopinavir;
  b. about 0.5 to about 1.5% by weight of hydroxypropylmethylcellulose;
  c. about 55 to about 65% by weight of oleic acid;
  d. about 4 to about 5% of stearic acid;
  e. about 0.1 to about 0.3% by weight of butylated hydroxytoluene;
  f. about 4 to about 6% by weight of mono diglyceride;
  g. about 5 to about 7% by weight of ceresin wax;
  h. about 9 to about 11% by weight of hydrogenated vegetable oil;
  i. about 1 to about 3% by weight of polyoxyl 100 stearate; and
  j. about 2 to about 4% by weight of glycerol monooleate;
wherein all % are by weight based upon the total weight of the composition In one embodiment, the composition contains lopinavir alone and comprises:
  a. about 11 to about 13% by weight of lopinavir;
  b. about 0.5 to about 1.5% by weight of hydroxypropylmethylcellulose;
  c. about 50 to about 60% by weight of oleic acid;
  d. about 4 to about 5% of stearic acid;
  e. about 0.1 to about 0.3% by weight of butylated hydroxytoluene;
  f. about 4 to about 6% by weight of mono diglyceride;
  g. about 5 to about 7% by weight of ceresin wax;
  h. about 9 to about 11% by weight of hydrogenated vegetable oil;
  i. about 1 to about 3% by weight of polyoxyl 100 stearate; and
  j. about 2 to about 4% by weight of glycerol monooleate;
wherein all % are by weight based upon the total weight of the composition.

In one embodiment, the composition the composition contains lopinavir alone and comprises:
  a. about 4 to about 6% by weight of lopinavir;
  b. about 0.5 to about 1.5% by weight of hydroxypropylmethylcellulose;
  c. about 55 to about 65% by weight of oleic acid;
  d. about 4 to about 5% of stearic acid;
  e. about 0.1 to about 0.3% by weight of butylated hydroxytoluene;
  f. about 4 to about 6% by weight of mono diglyceride;
  g. about 5 to about 7% by weight of ceresin wax;
  h. about 9 to about 11% by weight of hydrogenated vegetable oil;
  i. about 1 to about 3% by weight of polyoxyl 100 stearate; and
  j. about 2 to about 4% by weight of glycerol monooleate;
wherein all % are by weight based upon the total weight of the composition.

In one embodiment, the composition contains lopinavir alone and comprises:
a. about 5 to about 7% by weight of lopinavir;
b. about 0.5 to about 1.5% by weight of hydroxypropylmethylcellulose;
c. about 55 to about 65% by weight of oleic acid;
d. about 4 to about 5% of stearic acid;
e. about 0.1 to about 0.3% by weight of butylated hydroxytoluene;
f. about 4 to about 6% by weight of mono diglyceride;
g. about 5 to about 7% by weight of ceresin wax;
h. about 9 to about 11% by weight of hydrogenated vegetable oil;
i. about 1 to about 3% by weight of polyoxyl 100 stearate; and
j. about 2 to about 4% by weight of glycerol monooleate;
wherein all % are by weight based upon the total weight of the composition.

In one embodiment, the composition contains lopinavir and ritonavir and comprises:
a. about 0.9 to about 1.1% by weight of ritonavir;
b. about 9 to about 11% by weight of lopinavir;
c. about 0.5 to about 1.5% by weight of hydroxypropylmethylcellulose;
d. about 55 to about 65% by weight of oleic acid;
e. about 4 to about 5% of stearic acid;
f. about 0.1 to about 0.3% by weight of butylated hydroxytoluene;
g. about 4 to about 6% by weight of mono diglyceride;
h. about 5 to about 7% by weight of ceresin wax;
i. about 9 to about 11% by weight of hydrogenated vegetable oil;
j. about 1 to about 3% by weight of polyoxyl 100 stearate; and
k. about 2 to about 4% by weight of glycerol monooleate;
wherein all % are by weight based upon the total weight of the composition In one embodiment, the composition contains lopinavir and ritonavir and comprises:
a. about 0.9 to about 1.1% by weight of ritonavir;
b. about 11 to about 13% by weight of lopinavir;
c. about 0.5 to about 1.5% by weight of hydroxypropylmethylcellulose;
d. about 50 to about 60% by weight of oleic acid;
e. about 4 to about 5% of stearic acid;
f. about 0.1 to about 0.3% by weight of butylated hydroxytoluene;
g. about 4 to about 6% by weight of mono diglyceride;
h. about 5 to about 7% by weight of ceresin wax;
i. about 9 to about 11% by weight of hydrogenated vegetable oil;
j. about 1 to about 3% by weight of polyoxyl 100 stearate; and
k. about 2 to about 4% by weight of glycerol monooleate;
wherein all % are by weight based upon the total weight of the composition.

In one embodiment, the composition contains lopinavir and ritonavir and comprises:
a. about 0.4 to about 0.6% by weight of ritonavir;
b. about 4 to about 6% by weight of lopinavir;
c. about 0.5 to about 1.5% by weight of hydroxypropylmethylcellulose;
d. about 55 to about 65% by weight of oleic acid;
e. about 4 to about 5% of stearic acid;
f. about 0.1 to about 0.3% by weight of butylated hydroxytoluene;
g. about 4 to about 6% by weight of mono diglyceride;
h. about 5 to about 7% by weight of ceresin wax;
i. about 9 to about 11% by weight of hydrogenated vegetable oil;
j. about 1 to about 3% by weight of polyoxyl 100 stearate; and
k. about 2 to about 4% by weight of glycerol monooleate;
wherein all % are by weight based upon the total weight of the composition.

In one embodiment, the composition contains lopinavir and ritonavir and comprises:
a. about 0.4 to about 0.6% by weight of ritonavir;
b. about 5 to about 7% by weight of lopinavir;
c. about 0.5 to about 1.5% by weight of hydroxypropylmethylcellulose;
d. about 55 to about 65% by weight of oleic acid;
e. about 4 to about 5% of stearic acid;
f. about 0.1 to about 0.3% by weight of butylated hydroxytoluene;
g. about 4 to about 6% by weight of mono diglyceride;
h. about 5 to about 7% by weight of ceresin wax;
i. about 9 to about 11% by weight of hydrogenated vegetable oil;
j. about 1 to about 3% by weight of polyoxyl 100 stearate; and
k. about 2 to about 4% by weight of glycerol monooleate;
wherein all % are by weight based upon the total weight of the composition.

Preferred examples of such compositions are disclosed in Example 7.

Other Preferred Compositions

Creams are a preferred composition for use according to the invention. Compositions comprising lopinavir alone may be formulated as a cream and a lopinavir cream is disclosed in Example 8. It will be appreciated that such cream formulations may be adapted to contain both lopinavir and ritonavir.

Preferred Compositions—Lopinavir Only

In a preferred embodiment, the pharmaceutical composition of the invention comprises lopinavir as the sole Active Pharmaceutical Ingredient (API).

Conveniently, the pharmaceutical composition is an anhydrous composition. It has surprisingly been found that lopinavir exhibits greater chemical stability in an anhydrous pharmaceutical composition when compared to certain aqueous based pharmaceutical compositions. In one embodiment, the pharmaceutical composition comprises less than 5% by weight of water of the total pharmaceutical composition weight, such as less than 1% by weight, such as less than 0.5% by weight, such as less than 0.1% by weight, such as less than 0.05% by weight. In one embodiment, the pharmaceutical composition is substantially free of water. In one embodiment, the pharmaceutical composition is entirely free of water.

Suitable anhydrous compositions include non-aqueous emulsions, ointments, pastes, gels and rigid dosage forms such as pellets, solid or semi-solid stick compositions and lip-balms (including lip-balms contained in lipstick-style tubes).

Conveniently, the pharmaceutical composition is an ointment.

A preferred composition is a pharmaceutical composition comprising:
a. lopinavir as the sole Active Pharmaceutical Ingredient;
b. an unsaturated free fatty acid;
c. a stiffening agent; and
d. (optionally) additional excipients;

wherein the unsaturated free fatty acid is present at a level of at least 50% by weight of the total pharmaceutical composition weight and wherein the pharmaceutical composition is a solid or semi-solid at room temperature.

A yet further preferred composition is a pharmaceutical ointment composition comprising:
e. lopinavir as the sole Active Pharmaceutical Ingredient;
f. an unsaturated free fatty acid;
g. a stiffening agent; and
h. (optionally) additional excipients;
wherein the unsaturated free fatty acid is present at a level of at least 50% by weight of the total pharmaceutical composition weight and wherein the pharmaceutical composition is a semi-solid at room temperature.

In one embodiment, the pharmaceutical ointment composition comprises a high level of unsaturated free fatty acid, conveniently selected from 50% to 70% by weight of the total pharmaceutical composition weight, such as 55% to 65% by weight, such as 60% to 65% by weight of the total pharmaceutical composition weight. In one embodiment, the ointment composition comprises an unsaturated free fatty acid at a level of about 60% by weight of the total pharmaceutical composition weight, more conveniently about 62% by weight of the total pharmaceutical composition weight. Conveniently the unsaturated fatty acid selected from oleic acid, linoleic acid, alpha-linoleic acid, palmitoleic acid, gondoic acid, and ricinoleic acid. More conveniently, the solvent is oleic acid.

Advantageously, when present at a high level, it has been found that the unsaturated fatty acid can ensure the lopinavir is solubilised in the composition but can also act as a permeation enhancer at the site of application to aid and improve the delivery of lopinavir to the target site of activity. As shown in the Examples (e.g. Example 16), such a composition has been found to provide remarkable efficacy in treating HSV related conditions such as cold sores.

In a further embodiment, the ointment also comprises a high level of a stiffening agent. In a particular embodiment, the ointment comprises a high level of the stiffening agent, preferably selected from 15% to 30% by weight of the total pharmaceutical composition weight, such as 20% to 28% by weight, such as 23% to 26% by weight of the total pharmaceutical composition weight. In one embodiment, the ointment comprises a stiffening agent at a level of about 25% by weight of the total pharmaceutical composition weight, more conveniently about 25.8% by weight of the total pharmaceutical composition weight. Conveniently the stiffening agent is selected from capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, henatriacontylic acid, heptatriacontanoic acid and octatriacontanoic acid. The stiffening agent is preferably stearic acid.

In one embodiment, the unsaturated free fatty acid and the stiffening agent are present in the pharmaceutical composition in a weight ratio of unsaturated free fatty acid:stiffening agent in the range of 1:1 to 4:1, such as in the range of 1:1 to 3.6:1, such as in the range of 2:1 to 3:1, such as about 2:1, or such as about 2.4:1.

Suitable amounts of lopinavir in an ointment composition may be from about 0.1 to 30% by weight of the total pharmaceutical composition weight. In certain ointment compositions of the invention, it has been found that lopinavir exhibits good chemical and physical stability despite being present at high levels. It has been found that the improved stability may allow for room temperature storage of a lopinavir ointment based pharmaceutical composition of the invention. In one embodiment, lopinavir is stable within the pharmaceutical composition during a process to manufacture the pharmaceutical ointment composition. In one embodiment, lopinavir is stable within the pharmaceutical ointment composition during storage post-manufacture. In one embodiment, lopinavir is stable within the pharmaceutical ointment composition for at least 3 months, such as at least 6 months, such as at least 9 months, such as at least 12 months, such as at least 18 months, such as at least 24 months, or such as at least 36 months, at a temperature of 5° C., 25° C., 30° C. or at 45° C., and/or at a relative humidity of 60%, 65%, or 75% RH. In one embodiment, lopinavir is stable within the pharmaceutical ointment composition for at least 6 months, such as at least 9 months, such as at least 12 months, such as at least 18 months, such as at least 24 months, or such as at least 36 months, at ambient conditions.

Using lopinavir at a high loading provides the advantage of being able to administer the required dose in a small volume application. Conveniently, lopinavir is present in an ointment composition at a level of 5 to 30% by weight of the total pharmaceutical composition weight, such as 6 to 30% by weight, 7 to 30% by weight, 8 to 20% by weight, 9 to 15% by weight or 10 to 13% by weight of the total pharmaceutical composition weight. Conveniently, lopinavir is present in an ointment composition at a level of about 10, 11, 12, 13 or 14% by weight, preferably 12% by weight of the total pharmaceutical composition weight.

In one embodiment, lopinavir is present in a dissolved state in the pharmaceutical composition. It will be apparent to the skilled person that the active pharmaceutical ingredient is dissolved or dispersed within the pharmaceutical composition by the use of techniques such as optical microscopy using polarised light filters, differential scanning calorimetry or micro FTIR. For example, a placebo pharmaceutical composition (i.e., a composition containing no active pharmaceutical ingredients) can be spiked with a crystalline active pharmaceutical ingredient. When viewed under an optical microscope using polarised light filters, the crystalline active pharmaceutical ingredient will exhibit birefringence. Thus, the spiked placebo composition can be used as a comparison standard in order to confirm there is no crystalline active pharmaceutical ingredient in the pharmaceutical composition, and thereby demonstrating the active pharmaceutical ingredient is dissolved within the pharmaceutical composition. Alternatively, and/or additionally, micro FTIR can be used to confirm the active pharmaceutical ingredient is dissolved in the pharmaceutical composition. In this case, spectra obtained for a pharmaceutical composition spiked with the active pharmaceutical ingredient and for the pharmaceutical composition can be compared and used to demonstrate the active pharmaceutical ingredient is dissolved in the pharmaceutical composition.

In one embodiment, lopinavir and the unsaturated free fatty acid are present in the pharmaceutical composition in a weight ratio of lopinavir:unsaturated free fatty acid in the range of 1:4 to 1:6, such as in the range of 1:4.5 to 1.5.5, such as about 1:5, or such as about 1:5.17.

Optionally, additional excipients may be included in the lopinavir only ointment composition according to the present invention providing that inclusion of such excipients does not unacceptably impact the ability of the composition to be a semi-solid at room temperature.

Suitable additional excipients may be included in the composition include muco-adhesives, thickeners, blending agents and antioxidants.

In one embodiment, the pharmaceutical composition further comprises a muco-adhesive. A muco-adhesive is an excipient which adheres to a mucous membrane. In one embodiment, the muco-adhesive is selected from a non-ionic polymer and an ionic polymer selected from a cellulose ether and an ionic polymer.

In one embodiment, the pharmaceutical composition further comprises a thickener and/or a blending agent. A thickener is an excipient which when added to a mixture increases the viscosity of the mixture and for conferring the pharmaceutical composition with greater physical stability and/or control during delivery of the active pharmaceutical ingredient to the site of application. In one embodiment, the thickener is selected from mono di glyceride, ceresin wax, and hydrogenated vegetable oil. In one embodiment, the pharmaceutical composition comprises mono di glyceride, ceresin wax and hydrogenated vegetable oil. A blending agent is an agent which promotes uniformity within the pharmaceutical composition, for example it promotes uniformity for organoleptic attributes within the pharmaceutical composition. In one embodiment, the blending agent is selected from polyoxy 100 stearate and glycerol monooeleate.

In one embodiment, the pharmaceutical composition comprises an antioxidant. In one embodiment, the antioxidant is butylated hydroxytoluene or butylated hydroxyanisole. In one embodiment, the antioxidant is present in the pharmaceutical composition at about 0.05 to about 0.5% by weight of the total pharmaceutical composition by weight, such as about 0.05 to about 0.15% by weight, such as about 0.1 to about 0.3% by weight, such as about 0.2% by weight.

The inventors have found that certain ointment compositions exhibit high viscosity and beneficial rheological properties. Indeed, it has been found that certain ointment compositions containing lopinavir as the sole active pharmaceutical ingredient do not liquify at room temperature and are therefore surprisingly very well suited to being retained both topically and mucosally (even without the need for a mucoadhesive, such as hydroxypropylmethyl cellulose). In one embodiment, pharmaceutical ointment composition does not contain a muco-adhesive, such as hydroxypropylmethyl cellulose. In a further embodiment, pharmaceutical ointment composition does not contain a thickener such as a mono di glyceride, ceresin wax, and hydrogenated vegetable oil. In a particular embodiment, the pharmaceutical ointment composition does not contain a muco-adhesive or a thickener.

In one embodiment, the pharmaceutical ointment composition has a tan δ value of between about 0.5 and about 1.5 at 37° C., such as about 0.8 and about 1.2.

In one embodiment, the pharmaceutical ointment composition has a complex viscosity of between about 2000 and about 5000 cps when measured at 25° C. and 0.5% strain at an angular frequency of 0.1 rad/s, such as between about 2500 to about 4500 cps, such as between about 3500 and about 4500 cps through to between about 200 and about 600 cps when measured at 25° C. and 0.5% strain at an angular frequency of 1 rad/s, such as between about 300 to about 500 cps, such as between about 350 and about 450 cps. In a further embodiment, the pharmaceutical ointment composition has a complex viscosity of about 4000 cps when measured at 25° C. and 0.5% strain at an angular frequency of 0.1 rad/s through to about 400 when measured at 25° C. and 0.5% strain at an angular frequency of 1 rad/s. Complex viscosity is defined as the frequency-dependent viscosity function determined for a viscoelastic fluid by subjecting it to oscillatory shear stress. The rheological behavior of the composition can be tested according to the methodology described in Example 9.

Furthermore, certain ointment compositions containing lopinavir as the sole active pharmaceutical ingredient have been found to be highly homogeneous and can be prepared using a simple mixing process without the need for blending agents, high processing energy or heating. Such compositions possess a high degree of manufacturing consistency and low variability.

In a particular embodiment, the pharmaceutical ointment composition does not contain a muco-adhesive, a thickener or a blending aid, such as polyoxy 100 stearate and glycerol monooeleate.

In one embodiment, the process of preparing the ointment compositions of the invention comprises incorporating the stiffening agent, the at least one active pharmaceutical ingredient, and the unsaturated free fatty acid by low energy shear mixing.

Upon application at a site of application of, it has been found that components of certain lopinavir only ointments vanish rapidly leaving minimal or no visible residue. In one embodiment, the pharmaceutical ointment composition, upon topical application to a site of application, leaves minimal or no visible residue of the pharmaceutical composition at the site of application. In one embodiment, minimal or no visible residue is observed after at least 5 minutes from topical application, such as about 10 minutes. In one embodiment, the pharmaceutical composition upon topical application to skin is absorbed by the skin. In one embodiment, the pharmaceutical composition upon topical application to skin is absorbed by the skin leaving no visible residue.

A preferred composition is a pharmaceutical ointment composition comprising:
  a. about 9 to 15% by weight of lopinavir as the sole Active Pharmaceutical Ingredient;
  b. about 55% to 70% by weight of oleic acid;
  c. about 20% to 30% by weight of stearic acid; and
  d. about 0.05 to about 0.5% of an antioxidant;
  wherein all % are by weight based upon the total weight of the composition; and wherein the pharmaceutical composition is a semi-solid at room temperature.

A preferred composition is a pharmaceutical ointment composition comprising:
  a. about 9 to 15% by weight of lopinavir as the sole Active Pharmaceutical Ingredient;
  b. about 55% to 70% by weight of oleic acid;
  c. about 20% to 30% by weight of stearic acid; and
  d. about 0.05 to about 0.5% of an antioxidant;
  wherein all % are by weight based upon the total weight of the composition; and wherein the pharmaceutical composition is a semi-solid at room temperature.

A preferred composition is a pharmaceutical ointment composition comprising:
  a. about 9 to 15% by weight of lopinavir as the sole Active Pharmaceutical Ingredient;
  b. about 55% to 70% by weight of oleic acid;
  c. about 20% to 30% by weight of stearic acid; and
  d. about 0.05 to about 0.5% of an antioxidant;
  wherein all % are by weight based upon the total weight of the composition; and wherein the pharmaceutical ointment composition does not contain an additional muco-adhesive, a thickener or a blending aid; and wherein the pharmaceutical composition is a semi-solid at room temperature.

A preferred composition is a pharmaceutical ointment composition comprising:
a. about 10 to 13% by weight of lopinavir as the sole Active Pharmaceutical Ingredient;
b. about 57% to 65% by weight of oleic acid;
c. about 22% to 27% by weight of stearic acid; and
d. about 0.05 to about 0.5% of an antioxidant;
wherein all % are by weight based upon the total weight of the composition; and wherein the pharmaceutical ointment composition does not contain hydroxyproplyl methylcellulose; and wherein the pharmaceutical composition is a semi-solid at room temperature.

A preferred composition is a pharmaceutical ointment composition comprising:
a. about 10 to 13% by weight of lopinavir as the sole Active Pharmaceutical Ingredient;
b. about 57% to 65% by weight of oleic acid;
c. about 22% to 27% by weight of stearic acid; and
d. about 0.05 to about 0.5% of an antioxidant;
wherein all % are by weight based upon the total weight of the composition; and wherein the pharmaceutical ointment composition does not contain an additional muco-adhesive, a thickener or a blending aid; and wherein the pharmaceutical composition is a semi-solid at room temperature.

A preferred composition is a pharmaceutical ointment composition comprising:
a. about 12% by weight of lopinavir as the sole Active Pharmaceutical Ingredient;
b. about 62% by weight of oleic acid;
c. about 25% by weight of stearic acid; and
d. about 0.2% by weight of an antioxidant selected from butylated hydroxytoluene or butylated hydroxyanisole;
wherein all % are by weight based upon the total weight of the composition; and wherein the pharmaceutical composition is a semi-solid at room temperature.

A preferred composition is a pharmaceutical ointment composition comprising:
a. about 12% by weight of lopinavir as the sole Active Pharmaceutical Ingredient;
b. about 62% by weight of oleic acid;
c. about 25.8% by weight of stearic acid; and
d. about 0.2% by weight of an antioxidant selected form butylated hydroxytoluene or butylated hydroxyanisole;
wherein all % are by weight based upon the total weight of the composition; and wherein the pharmaceutical ointment composition does not contain hydroxyproplyl methylcellulose; and wherein the pharmaceutical composition is a semi-solid at room temperature.

A preferred composition is a pharmaceutical ointment composition consisting:
a. about 12% by weight of lopinavir as the sole Active Pharmaceutical Ingredient;
b. about 62% by weight of oleic acid;
c. about 25.8% by weight of stearic acid; and
d. about 0.2% by weight of an antioxidant selected form butylated hydroxytoluene or butylated hydroxyanisole;
wherein all % are by weight based upon the total weight of the composition; and wherein the pharmaceutical composition is a semi-solid at room temperature.

Dosing

It will be appreciated that the amount of lopinavir alone; or lopinavir and ritonavir required is determined by biological activity and bioavailability, which in turn depends, in part, on the precise mode of administration, the physicochemical properties of the composition employed, and whether the compositions are being used as a monotherapy or in a combined therapy with other oral or topical medicines. Indeed, it is also possible that at least one active pharmaceutical ingredient could be topically applied in addition to oral dosing of the same compounds or other active pharmaceutical ingredient(s). The frequency of administration will also be influenced by the abovementioned factors and particularly the half-life of the active pharmaceutical ingredients within the subject being treated.

Daily doses may be given in the form of a paste, cream, lotion, a solid or semi-solid stick composition, a lip-balm (including a lip-balm contained in a lipstick-style tube), ointment or similar compositions for topical administration and be applied to the skin once daily, twice daily, thrice daily or as many times per day as a clinician deems necessary.

Preferably the composition is a paste, cream, lotion, ointment or similar composition for topical administration comprising an unsaturated free fatty acid; a stiffening agent (as defined above); and lopinavir alone or lopinavir and ritonavir in a weight ratio of between 9:1 and 18:1.

In a particular embodiment, the composition is a paste, cream, lotion, a solid or semi-solid stick composition, a lip-balm (including a lip-balm contained in a lipstick-style tube), an ointment or similar composition for topical administration comprising an unsaturated free fatty acid; a stiffening agent (as defined above); and lopinavir alone as the sole Active Pharmaceutical Ingredient. Conveniently, the composition is an ointment or similar anhydrous composition for topical administration comprising an unsaturated free fatty acid; a stiffening agent (as defined above); and lopinavir alone as the sole Active Pharmaceutical Ingredient.

In one embodiment, topical treatment regimens for HSV lesions may range from intermittent or continuous application and may continue until the lesion has disappeared or receded to a clinician satisfaction. In the case of a cold sore treatment may only be required for several days (e.g. 3 or 4 days) although the treatment of genital or anal herpes may require long treatment regimens (e.g. between 1 and 16 weeks—depending on the type and severity of lesions).

Cold sores may be treated with a composition which is applied to the affected area at least once a day and preferably twice a day in an amount sufficient to cover the lesion. In a preferred embodiment, cold sores may be treated with a composition which is applied to the affected area 3 or 4 times a day. In a particularly preferred embodiment, in the case of a cold sore treatment, application is only required for up to 3 days, conveniently up to 2 days, yet more conveniently just a single day. In a preferred embodiment, cold sores may be treated with only one course of treatment.

The composition may be applied directly to the lesion and the treatment area may include a margin around the lesion (e.g. 0.5 cms for a cold sore).

Optimal dosages to be administered may be determined by those skilled in the art, and will vary with the strength of the preparation, the mode of administration, and the advancement of the disease condition. Additional factors depending on the particular subject being treated will result in a need to adjust dosages, including, for example, subject age, weight, diet, and time of administration.

Compositions according to the invention may be rubbed into the lesion and left exposed to the air. Alternatively, the compositions may be applied and covered by a dressing (as known to the art) to keep the composition in place and occlude the composition from the air and/or contaminating clothing.

The medicament may be administered to a subject for as long as treatment is required. The length of time for which treatment will be required will depend upon the exact condition being treated or prevented and its severity. A skilled person will appreciate that treatment should be maintained in view of a number of factors which will include any requirement to eradicate HSV; to reduce or eradicate cells with an abnormal phenotype; or to shrink or eradicate a lesion.

In preferred embodiments an ointment disclosed in Example 6 or Example 9 or a cream disclosed in Example 7 may be topically applied to a cold sore 3 or 4 time a day. Between 0.01 g and 1.0 g of the ointment or cream may be applied to a 1×1 cm site (lesion+a margin).

In a further aspect, there is provided a kit of parts, the kit comprising instructions for use and a tube comprising the pharmaceutical composition of the first aspect. In one embodiment, the tube is an aluminum tube.

EXAMPLES

Materials & Methods Utilised in Examples 1-6

Cell Culture; Telomerase immortalised N-Tert human foreskin Keratinocyes were maintained in standard T-75 tissue culture flasks (Corning, USA) in 25 ml of Keratinocyte serum-free medium (KSFM) supplemented with L-glutamine, 0.2 ng/ml epidermal growth factors (EGF) and 25 µg/mL bovine pituitary extract (BPE) (Gibco, Invitrogen, UK). These were maintained at 37° C. in a humidified atmosphere of 5% $CO_2$ and the medium was changed every 2 days as required. For routine sub-culture the medium was aspirated, cells washed with PBS (Gibco-Invitrogen, UK) and 2 ml of Cell Culture Grade Trypsin 0.05% solution with EDTA (Gibco-Invitrogen, UK) added to each flask which was incubated at 37° C./5% $CO_2$ for 10 minutes. A 10 ml aliquot of KSFM plus 10% foetal bovine serum (FBS) (Gibco-Invitrogen, UK) was then added and the cells centrifuged at 6000 g for 6 minutes. The medium was aspirated and cells washed with 10 mls of PBS (Gibco Invitrogen, UK) followed by re-suspension in 10 mls of fresh KSFM and final a cell count carried out.

HSV1 & 2 Replication Assays; T25 flasks (Corning, USA) were each seeded with 600,000 N-Tert cells in serum-free KSFM plus supplements and incubated at 37° C./5% $CO_2$ until confluent (Approximately 72 hours). The medium was then aspirated and cells infected with either 25 µl aliquot of HSV2 strain HG52, 1 µl of HSV1 strain 17+ or a 5 µl aliquot of the acyclovir resistant HSV2 strain 132349 ACV-res (Public Health England, Porton Down, UK) in 0.5 ml of serum-free KSFM plus supplements for a period of 2 hours at 37° C./5% $CO_2$. The volume of each HSV strain stock used was empirically determined as the amount required to produce pronounced cytopathic changes in infected control flasks over the time course of the experiment. A 9.5 ml aliquot of KSFM plus supplements was then added to each flask and cells infected with the HG52 or 17+ strains incubated overnight whereas cell infected with the 132349 ACV-res strain were incubated for 5 hours at 37° C./5% $CO_2$. Stock solutions of each active pharmaceutical ingredient (API) were freshly prepared every week from dry powder (Douglas Pharna, NZ) dissolved volumetrically in DMSO at 100 mM and stored at −20° C. Appropriate final dilutions of these API stocks solutions were made in KSFM plus supplements such that the same volume of DMSO (2 µl) was added to each infected flask. Where mixed APIs were used, concentrations were calculated as w/w ratios. API treated HSV2 HG52 infected cells were then incubated for 48 hours, HSV1 17+ infected cells were incubated for 8 hours and HSV-2 132349 ACV-res infected cells were incubated for 12 hours prior to harvesting for immunostaining. A concentration of 5 µM Acyclovir (VWR International, UK) was also added as a comparator to flasks infected with HSV-2 132349 ACV-res in order to verify the acyclovir resistant nature of the strain. Previous studies have shown that >100 µM of Acyclovir is required for toxicity against this strain whereas <0.8 µM proved very effective against the HSV1 17+ strain (See Table 2 in Houston et al (2017) PLoS ONE 12(6); e01799291).

Harvesting & Immunostaining; Growth medium was decanted from each flask and placed into 15 ml universal tubes (Corning, USA) and the cells rinsed with 1 ml of 1×PBS which was pooled with the growth medium. A 1 ml aliquot of NB Cell Culture Grade Trypsin 0.05% solution with EDTA was added to each T-25 flask and cells incubated at 37° C./5% $CO_2$ for 10 minutes. A 1 ml aliquot of FBS was added to the decanted growth medium plus PBS from the previous step and 2 ml of this was then added to each flask to inactivate the trypsin. The trypsinised cells were then pooled with the decanted growth medium and an aliquot taken for analysis of cell viability using Via-1 cassette NC3000 cell cytometer assays (CheoMetec A/S, Denmark). The remaining cells were centrifuged at 6000 g for 5 minutes, the medium aspirated and the cells re-suspended and washed with 10 ml of PBS followed by re-centrifugation. Finally the cells were re-suspended in 70% of ice-cold ethanol, stored overnight at 4° C. and a volume containing 60,000 cells was aliquoted into 1.5 ml Eppendorf tubes and centrifuged for 5 minutes at 5000 rpm. The supernatant was aspirated and pellets re-suspended in 300 µl of PBS/0.5% Bovine Serum Albumin (BSA) (w/v) and centrifuged onto single Shandon™ Cytoslides™ (Thermo, UK) using a Cellspin 1 Cytocentrifuge (Tharmac, Germany) at 800 rpm for 4 min. Slides were then air dried, fixed for 20 min in 100% ice-cold methanol and washed once in PBS-T (PBS/0.05% (v/v) Tween-20) buffer for 5 minutes. Enough protein blocking solution (DAKO, UK) to cover the cells was then dripped onto the slides which were incubated at room temperature for 30 minutes followed by ×2 washes in PBS-T for 5 minutes. Anti HSV½ ICP5 major capsid primary antibody (Abcam ab6508) was then applied to each slide at a concentration of 1:100 in PBS-BSA and incubated overnight at 4° C., followed by 1 hour at 37° C. Slides were then washed twice in PBS-T for 10 minutes before DAB staining with an Envision kit according to the manufacturer's instructions (DAKO, UK). Briefly cells were incubated with the supplied stock solution of HRP-conjugated anti-Rabbit/Mouse secondary antibody at room temperature for 30 minutes. These were then washed three times in PBS-T buffer for 5 minutes each and DAB Substrate Chromagen solution applied for 10 minutes at room temperature followed by quenching in PBS-T and counterstaining with 50% Haematoxylin (Sigma, UK) for 20-30 seconds. Slides were stored in PBS-T overnight at 4° C. and were then dehydrated through 30%, 50%, 75% & 90% ethanol before immersion in xylene and mounting in DPX (Sigma, UK).

Image Analysis; HSV immuno-stained cells were photographed using a Nikon Eclipse E600 microscope where positive cells stained brown (DAB) whereas negative cells only stained blue (haematoxylin). Multiple images were randomly selected for each treatment and recorded in JPG format. Image analysis was carried out using a bespoke Python program and digital arrays were processed generally using the OpenCV package. After reshaping through Numpy, RGB pixels were clustered based on the Kmeans algorithm and the colour from each stain type was extracted via the labeled pixels. The percentage HSV positive DAB staining was then estimated by calculating the ratio of array shapes which stained in brown compared to the total stain (brown+blue).

Cytotoxicity Assay; The percentage of live versus dead cells was determined using Via-1 cassette NC3000 cell cytometer assays as described in the preceding Harvesting and Immunostaining section where uninfected cells were exposed to treatment with the various APIs for a period of 48 hours prior to harvesting. Each data point was the result of four separate Via-1 assays.

Example 1: Activity of Lopinavir Only and 12:1 (W/W) Lopinavir: Ritonavir Against HSV2 Replication FIG. 1A shows phase contrast images of the effects of HSV2 infection on the morphology of N-Tert keratinocytes exposed to either DMSO control or 20 µM lopinavir for 48 hours. The cytopathic effects of the virus are clearly visible in the DMSO treated HSV2 infected cells, when compared to uninfected controls. However, HSV2 infected cells treated with 20 µM lopinavir showed virtually no cytopathic effects.

FIG. 1B shows images of anti-HSV antibody immunostaining of these cells which confirmed that the majority of DMSO treated HSV2 infected cells stained strongly positive for the virus with no signal present in the control virus negative cells. Very few HSV2 positive cells were seen in infected cells exposed to 20 µM lopinavir for 48 hours.

FIG. 1C shows quantitative analysis of the percentage of HSV2 positive cells detected by immune staining. Three separate random images were analysed for each treatment which demonstrated that 20 µM lopinavir only and 20 µM 12:1 w/w Lop/Rit both caused a marked reduction in the percentage of virus positive cells.

Example 2: Activity of 12:1 w/w Lop/Rit and Nelfinavir Against HSV2 Replication

The inventors were surprised to find that Lopinavir (alone or with ritonavir) cleared virus when the prior art (Gantt et al. (supra)) suggested these compounds would be ineffective, but the HIV protease inhibitor nelfinavir may possess activity against HSV. The inventors therefore compared the activity of the nelfinavir to a 12:1 (w/w) lopinavir:ritonavir composition they had used when researching the efficacy of these APIs in cancer therapy (the unpublished work discussed above)

Figure 2:
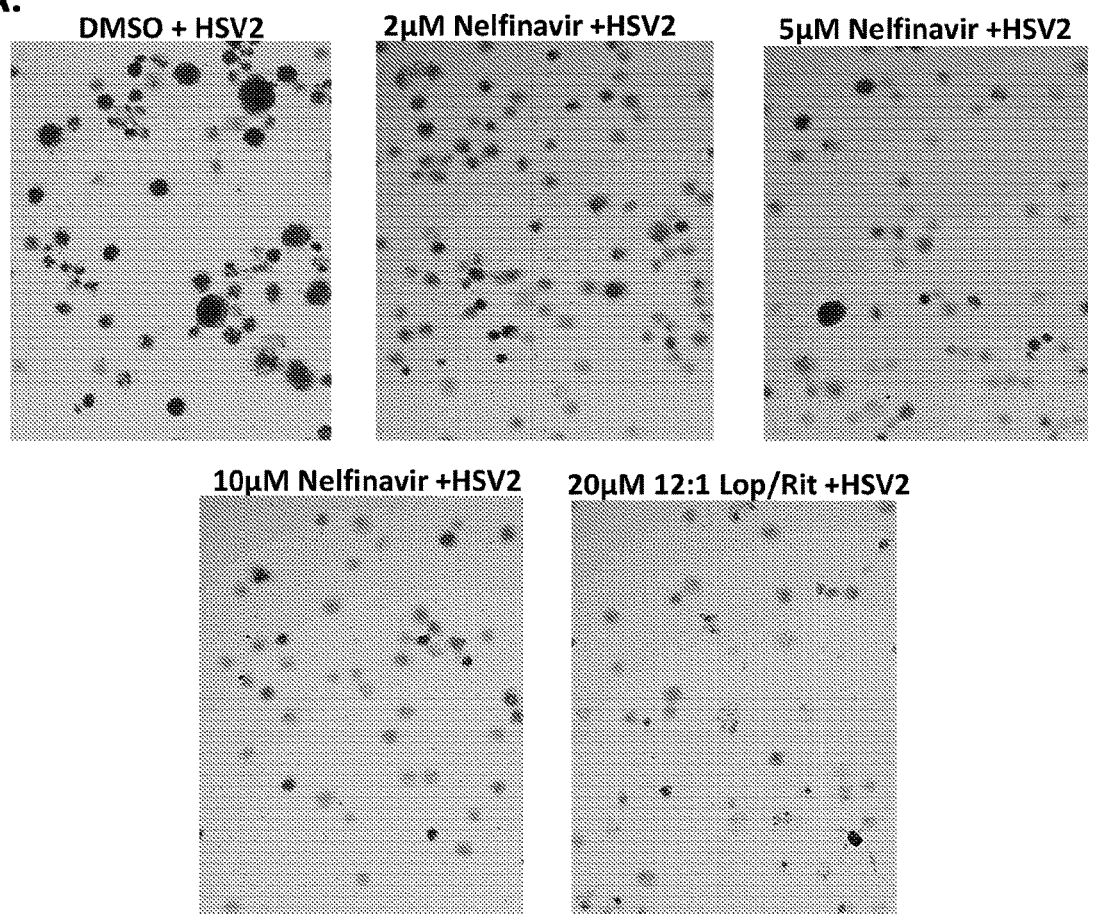
FIG. 2.
Figure 2:
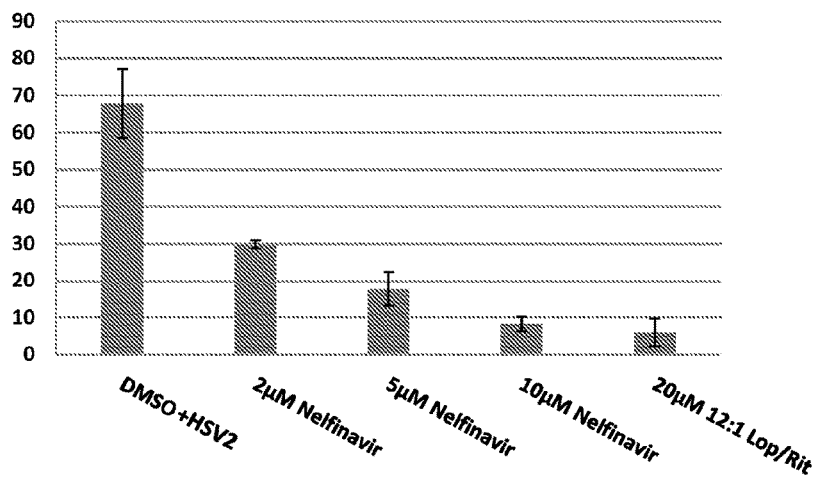

FIG. 2A shows representative images of anti-HSV immune-stained HSV2 infected N-Tert keratinocytes treated with the indicated concentrations and mixtures of the different APIs. Three separate images were analysed for each treatment.

FIG. 2B shows that 2 µM and 5 µM nelfinavir were less effective against HSV2 replication than 10 µM nelfinavir which was as effective as 20 µM 12:1 Lop/Rit.

Example 3: Toxicity of Lopinavir Only, Lop/Rit and Nelfinavir in Virus-Negative N-Tert Cells The inventors had noted that nelfinavir appeared to cause some toxicity toward N-Tert host cells and decided to analyse toxicity.

FIG. 3 shows Via-1 cassette viability assays on uninfected N-Tert keratinocytes treated for 48 hours with the indicated concentrations and mixtures of APIs shown. It can be seen that up to 25 µM of either lopinavir only or 12:1 (w/w) lopinavir:ritonavir at 20 µM had minimal toxic effects against these cells whereas 10 µM nelfinavir showed marked toxicity (reducing cell viability to <60%) and 20 µM nelfinavir showed even greater toxicity reducing cell viability to about 40%.

CONCLUSIONS

These results indicate that 20 µM of either lopinavir or 12:1 w/w Lop/Rit were more effective against HSV2 replication than either 2 or 5 µM nelfinavir and were equally as effective as 10 µM nelfinavir. However, 10 µM nelfinavir shows much greater non-specific toxicity in non-infected cells and, contrary to the teaching of the prior art, makes lopinavir alone or compositions comprising lopinavir and ritonavir much better choices for treating HSV infection.

Example 4: Activity of 12:1 w/w Lop/Rit and Nelfinavir Against HSV1 Replication

In view of the results obtained with HSV2 (Examples 1-3) the inventors investigated the effects of these compounds on HSV1 replication. Since pilot experiments showed that the HSV1 strain 17+ replicated at least five times faster than the HSV2 HG52 strain, the infection and treatment times were adjusted accordingly (See Materials & Methods).

FIG. 4A illustrates representative images of anti-HSV1 immune-stained HSV1 infected N-Tert keratinocytes treated with the indicated concentrations and mixtures of the different APIs. Three separate images were analysed for each treatment.

FIG. 4B shows that 2 µM and 10 µM nelfinavir both had very modest effects on HSV1 replication with the latter showing the most activity. However, 20 µM 12:1 w/w Lop/Rit had much greater activity against HSV1 replication than either concentration of nelfinavir and yet this concentration of Lop/Rit was far less toxic in virus negative cells (See FIG. 3).

Example 5: Activity of Lopinavir Only, Lop/Rit and Nelfinavir Against HSV1 Replication The results shown in FIG. 4B indicated that approaching 100% of DMSO treated cells were positive for HSV1 using the infection conditions. Based on this observation, it was decided to reduce the pre-treatment overnight virus incubation time by 2 hours prior to the addition of APIs. This was done to increase the numbers of cells in the earlier stages of viral replication which may be more susceptible to drug intervention. Accordingly, the work illustrated in this Example was conducted with a reduced incubation time compared to Example 4.

FIG. 5A illustrates representative images of anti-HSV immuno-stained HSV1 infected N-Tert keratinocytes treated with the indicated concentrations and mixtures of the different APIs. Three separate images were analysed for each treatment.

FIG. 5B demonstrated that the 2 hour reduction in the overnight pre-treatment virus incubation time reduced the total percentage of virus positive cells detected in the DMSO control by approximately half. Using these conditions, treatment with 2 or 10 µM nelfinavir had no discernible effect on HSV1 replication whereas 20 µM lopinavir as a single agent had by far the greatest activity. Analysis of the effects of 20 µM standard Kaletra formulation (4:1 w/w Lop/Rit) on HSV1 replication showed this had some activity although 20 µM of the 12:1 w/w Lop/Rit formulation was clearly more effective.

Example 6: Comparison of the Activity of Lopinavir and Acyclovir Against the Replication of Acyclovir Resistant HSV2

Initial range finding experiments with the acyclovir resistant HSV2 strain 132349 ACV-res, showed this to have a more rapid rate of replication than the HG52 or 17+ strains used in FIGS. 1, 2, 4 & 5. For this reason the post-infection incubation time was again reduced from overnight, as used for HG52 and 17+, to 5 hours for 132349 ACV-res after which APIs were added and the cells then incubated overnight.

FIG. 6A illustrates representative images of anti-HSV immuno-stained acyclovir resistant HSV2 infected N-Tert keratinocytes treated with the indicated concentrations of the different APIs. Three separate images were analysed quantitatively for each treatment.

Figure 5:
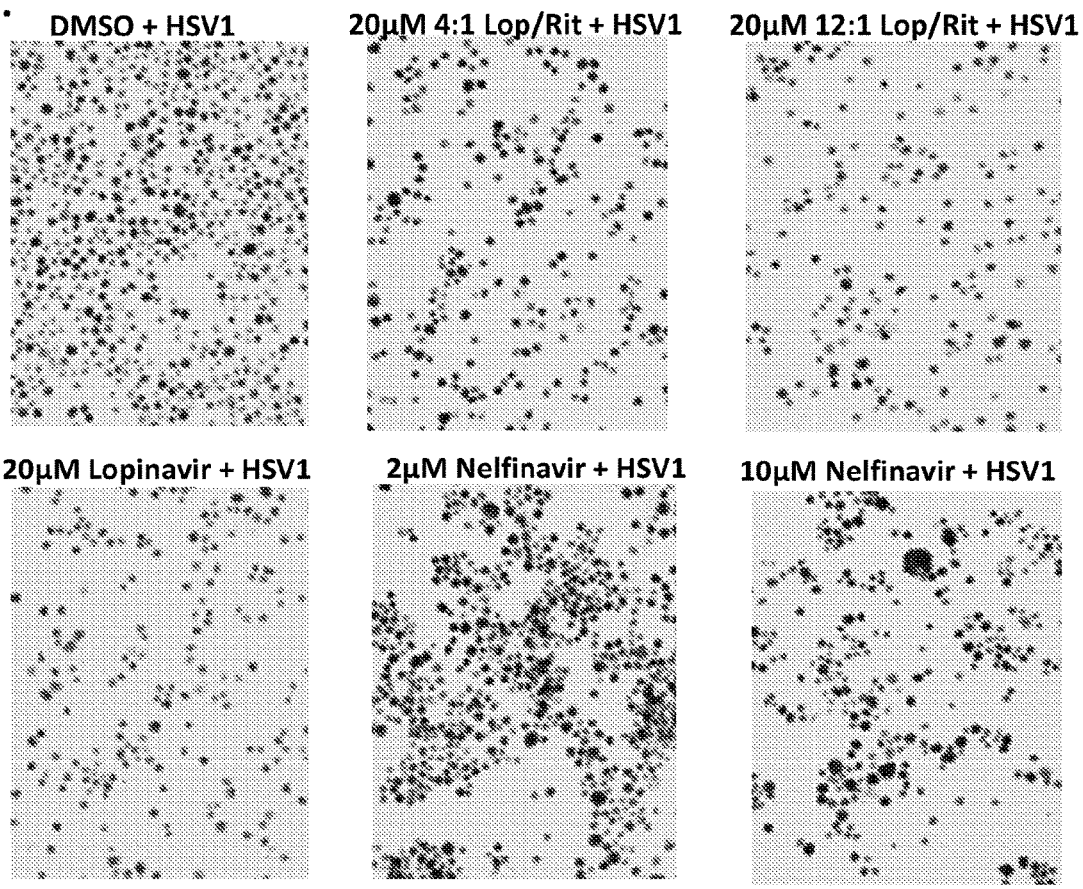
FIG. 5.
Figure 5:
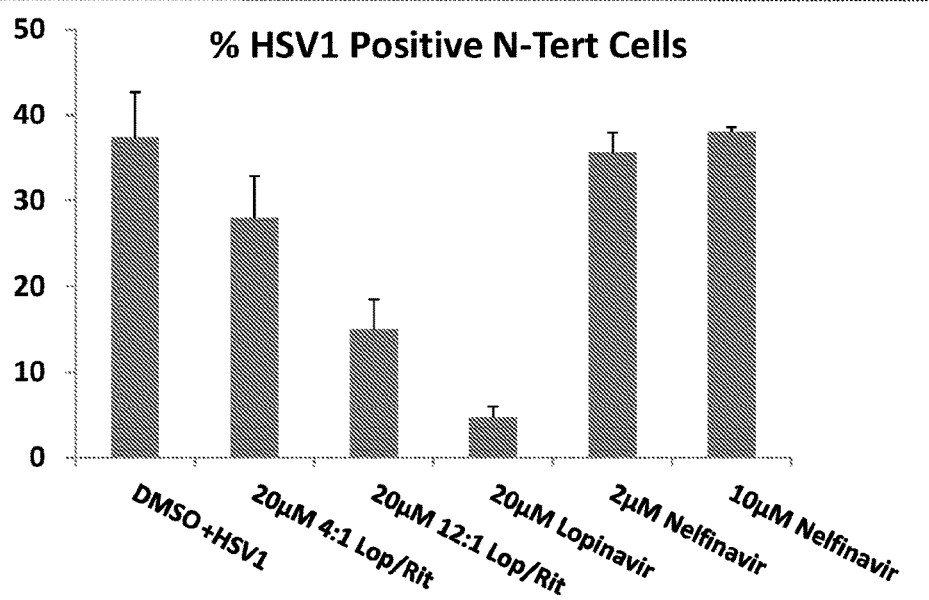

FIG. 6B shows that over the time course of the experiment, the acyclovir resistant HSV2 DMSO positive control produced a 50% infection rate which is comparable to that obtained with HSV1 17+ shown in FIG. 5. Treatment of Ac Res HSV2 infected cells with 504 of Acyclovir did not, as expected reduce the number of virus positive cells. However 504 of Acyclovir did unexpectedly cause a very significant-30% increase in the percentage of virus positive cells when compared to the DMSO control. In contrast, treatment of Ac Res HSV2 cells with either 10 µM or 20 µM lopinavir caused a pronounced drop in the number of virus positive cells to 10% and 5% respectively.

Overall Conclusions (Examples 1-6)

Lopinavir as a single agent and compositions comprising lopinavir and ritonavir represent new treatments for reducing the replication of HSV1 and HSV2 which are superior to nelfinavir since:
  (A) They are more effective than nelfinavir at its optimal dose; and
  (B) showed more specific anti-viral activity combined with much less non-specific toxicity than nelfinavir in non-infected cells.

Lopinavir as a single agent and compositions comprising lopinavir and ritonavir represent new treatments for reducing the replication of AR HSV. Accordingly conditions according to the invention are particularly useful for treating conditions caused by or associated with AR HSV infection.

Example 7: Preparation of Ointments for Use According to the Invention

For all formulations present below, all materials used are pharmaceutical grade (either US Pharmacopeia or European Pharmacopeia) except for white ceresin wax, which is Japanese Pharmaceutical Excipient grade.

The manufacture of compositions comprising both lopinavir and ritonavir which may be used according to the invention is described below in accordance with Tables 1-4.
  i. Add into the mixer the following materials—3, 4, 5, 6, 7, 8,9,1,10, 11 (if required)
  ii. Exclude air from the interior of the vessel
  iii. Heat to 70° C. while low shear mixing, to achieve a clear, transparent melt.
  iv. Add into the mixer the following material—2
  v. Exclude air from the interior of the vessel
  vi. Mix via low shear, to finely disperse the HPMC within the melt
  vii. Reduce the content temperature to 45° C. while low shear mixing
  viii. Discharge to storage vessel and exclude air during storage.
  ix. Pack composition into aluminium tubes, suitable for dispensing 1.0-5.0 g of composition. Aluminium tubes may contain a volume of 20-50 mls of composition.

TABLE 1

| # | Ingredient | Function(s) | % w/w |
|---|---|---|---|
| 1 | Oleic acid | Unsaturated free fatty acid | 62.823 |
| 2 | Hypromellose 2208 (4000 cps) | Muco-adhesive | 1.00 |
| 3 | Mono di glycerides (type 1) | Thickener | 5.00 |
| 4 | White ceresin wax | Thickener | 6.00 |
| 5 | Hydrogenated vegetable oil (type 1) | Thickener | 10.00 |
| 6 | Polyoxyl 100 stearate | Blending agent | 2.00 |
| 7 | Stearic acid | Stiffening agent | 4.50 |
| 8 | Glycerol monooleate | Blending agent | 3.00 |
| 9 | Butylatedhydroxytoluene | Antioxidant | 0.20 |
| 10 | Lopinavir | API | 5.000 |
| 11 | Ritonavir | API | 0.4775 |
|  |  | TOTAL | 100.000 |

TABLE 2

| # | Ingredient | Function(s) | % w/w |
|---|---|---|---|
| 1 | Oleic acid | Unsaturated free fatty acid | 57.345 |
| 2 | Hypromellose 2208 (4000 cps) | Muco-adhesive | 1.00 |
| 3 | Mono di glycerides (type 1) | Thickener | 5.00 |
| 4 | White ceresin wax | Thickener | 6.00 |
| 5 | Hydrogenated vegetable oil (type 1) | Thickener | 10.00 |
| 6 | Polyoxyl 100 stearate | Blending agent | 2.00 |
| 7 | Stearic acid | Stiffening agent | 4.50 |
| 8 | Glycerol monooleate | Blending agent | 3.00 |
| 9 | Butylatedhydroxytoluene | Antioxidant | 0.20 |
| 10 | Lopinavir | API | 10.000 |
| 11 | Ritonavir | API | 0.9550 |
|  |  | TOTAL | 100.000 |

TABLE 3

| # | Ingredient | Function(s) | % w/w |
|---|---|---|---|
| 1 | Oleic acid | Unsaturated free fatty acid | 61.800 |
| 2 | Hypromellose 2208 (4000 cps) | Muco-adhesive | 1.00 |
| 3 | Mono di glycerides (type 1) | Thickener | 5.00 |
| 4 | White ceresin wax | Thickener | 6.00 |
| 5 | Hydrogenated vegetable oil (type 1) | Thickener | 10.00 |
| 6 | Polyoxyl 100 stearate | Blending agent | 2.00 |
| 7 | Stearic acid | Stiffening agent | 4.50 |
| 8 | Glycerol monooleate | Blending agent | 3.00 |
| 9 | Butylatedhydroxytoluene | Antioxidant | 0.20 |
| 10 | Lopinavir | API | 6.000 |
| 11 | Ritonavir | API | 0.500 |
|  |  | TOTAL | 100.000 |

TABLE 4

| # | Ingredient | Function(s) | % w/w |
|---|---|---|---|
| 1 | Oleic acid | Unsaturated free fatty acid | 55.300 |
| 2 | Hypromellose 2208 (4000 cps) | Muco-adhesive | 1.00 |
| 3 | Mono di glycerides (type 1) | Thickener | 5.00 |
| 4 | White ceresin wax | Thickener | 6.00 |
| 5 | Hydrogenated vegetable oil (type 1) | Thickener | 10.00 |
| 6 | Polyoxyl 100 stearate | Blending agent | 2.00 |
| 7 | Stearic acid | Stiffening agent | 4.50 |
| 8 | Glycerol monooleate | Blending agent | 3.00 |
| 9 | Butylatedhydroxytoluene | Antioxidant | 0.20 |
| 10 | Lopinavir | API | 12.000 |
| 11 | Ritonavir | API | 1.000 |
|   |   | TOTAL | 100.000 |

Example 8: Preparation of a Cream Formulation for Use According to the Invention For all formulations present below, all materials used are pharmaceutical grade (either US Pharmacopeia or European Pharmacopeia) except for white ceresin wax, which is Japanese Pharmaceutical Excipient grade.

The manufacture of a cream comprising lopinavir (and optionally ritonavir) which may be used according to the invention is described below in accordance with Table 5.

i. Into main vessel add 1, 2, 3, 4, 5
  ii. For active batches, exclude air from the interior via vacuum −80 kPa. Replace with nitrogen. (×3) (N/A for placebo batches)
  iii. Heat the contents to 75° C., mixing as required until clear solution e.g. 60 rpm, homogenizer 600 rpm
  iv. Reduce the contents to 65° C., with stirring e.g. 60 rpm
  v. In a beaker dissolve 6 and 7 into 8 then add to side melter along with 9, 10, 11, 12, heating to 65° C. with stirring (fixed speed)
  vi. Introduce the side melter content into main vessel stirring at 60 rpm
  vii. For active batches, exclude air from the interior via vacuum −80 kPa. Replace with nitrogen (×3) (N/A for placebo batches)
  viii. Homogenize the emulsion e.g. stirrer 60 rpm, homogenizer 1500 rpm for 10 minutes
  ix. Cool content to at least below 30° C., mixing as required e.g. 60 rpm
  x. Discharge the product into HDPE bag lined polypail, well labelled.

TABLE 5

| # | Ingredient | MP ° C. | Function(s) | % w/w | g/batch |
|---|---|---|---|---|---|
| 1 | Oleic acid ** | 13 | Unsaturated free fatty acid | 20.00 | 400.0 |
| 2 | Stearic acid | 69 | Stiffening agent | 10.00 | 200.0 |
| 3 | White ceresin wax | ~65 | Thickener | 5.00 | 100.0 |
| 4 | Butylatedhydroxytoluene | 70 | Antioxidant | 0.10 | 2.0 |
| 5 | Lopinavir** | 124 | API | 5.00 | 100.0 |
| 6 | Methylparaben | N/A | preservative | 0.04 | 0.8 |
| 7 | Propylparaben | N/A | preservative | 0.01 | 0.2 |
| 8 | Propylene glycol | N/A | humectant | 2.00 | 40.0 |
| 9 | Sodium Lauryl Sulphate | N/A | surfactant | 3.00 | 60.0 |
| 10 | PEG-35 castor oil (cremophor EL) | N/A | surfactant | 5.00 | 100.0 |
| 11 | Sodium hydroxide | N/A | pH adjst | 0.00 | 0.0 |
| 12 | Purified water | N/A | Aqueous phase | 49.85 | 997.0 |
|   |   |   | TOTAL | 100.0 | 2000.00 |

Stability Studies

The composition according to Table 5 was tested for chemical stability for 3 months and the results are presented in Table 5a below. The formulation was stored under different stability conditions, and subsequently analysed. Based on the data generated, to achieve stability beyond 3 months, cold storage (5° C.) may be required.

TABLE 5a

Lopinavir Impurity Profile

| Relative Retention Time (RRT) relative to lopinavir | Time Zero 5° C. % Impurity | 3M 25° C./60% RH % Impurity | 3M 40° C./75% RH % Impurity |
|---|---|---|---|
| 0.28 | 0.01 | 0.03 | 0.33 |
| 0.65 | 0.12 | 0.25 | 0.48 |
| 1.10 | 0.03 | 0.03 | 0.08 |
| 1.17 | 0.03 | ND | 0.06 |
| 1.65 | ND | ND | ND |
| Total Unspecified | 0.07 | 0.17 | 0.38 |
| Total Impurities | 0.19 | 0.31 | 0.95 |

Note:
ND means not detected.

The following analytical methodology was used to analyse the formulation.

UHPLC:

Equipment Parameters:

| System Description | Waters Acquity H-Class UHPLC with a UV-VWD or UV-PDA detector (or equivalent) | |
|---|---|---|
| Column | Acquity BEH 300 C4, 2.1 mm × 100 mm, 1.7 µm (or equivalent) | |
| Column Temperature | 50° C. | |
| Detector Wavelength | 215 nm | |
| Flow Rate | 0.5 mL/min | |
| Injection Volume | 2 µL | |
| Sampling Rate | 5 points/sec | |
| Inject Wash | Post-inject: 6 seconds | |
| Integration | Peak area | |
| Run Time | About 30 mins | |
| Retention Time | Lopinavir: about 11 minutes (215 nm) | |
| Mobile phase A | Aqueous component of mobile phase A | To prepare 1 L: Dissolve 3.8 g of potassium dihydrogen phosphate and 0.25 g di-potassium hydrogen phosphate in 1000 mL of water. Filter through a 0.2 µm membrane filter (e.g. Millipore 0.2 µm GNWP). |
|  | Organic component of mobile phase A | Prepare an 18:8:5 mixture of acetonitrile/tetrahydrofuran/ 1-butanol. |

-continued

| | | |
|---|---|---|
| | Mobile phase A | Prepare a 25:75 mixture of organic component for mobile phase/filtered buffer A, and adjust the pH to 6.3 ± 0.05 with either 1M phosphoric acid or 1M potassium hydroxide. Degas by sonication |
| Mobile phase B | | Prepare a 10:90 mixture of tetrahydrofuran/acetonitrile. |
| Diluent | | Prepare a 2.5:47.5:50 mixture of 1-butanol/acetonitrile/buffer B (Buffer B: To prepare 1 L: Dissolve 4.1 g of potassium dihydrogen phosphate in 1000 mL of water.) |
| Sample preparation | | Sample Stock Solution (3000 µg/mL Lopinavir) Weigh about 3000 mg of KORU 2 Cream 5% W/W into a 50 mL volumetric flask. Pipette 2.5 mL of 1-butanol and 10 mL of acetonitrile into the flask and shake vigorously to disperse the ointment completely. Using a Pasteur pipette, rinse the neck and walls of flask with further 10 mL of acetonitrile and sonicate for 10 minutes with occasional swirling. Allow to equilibrate to room temperature prior to making up to volume with acetonitrile. Chill in fridge for 30 minutes. Sample Working Solution (1500 µg/mL Lopinavir) Transfer an aliquot (~10 mL) of chilled sample stock solution into a capped centrifuge tube and centrifuge the sample at 4000 RPM, for 5 minutes. Pipette 2.5 mL of supernatant, 2.5 mL of buffer B and 10 mL of n-heptane* into a capped centrifuge tube mix well by inversion to form an emulsification and centrifuge once more at 4000 RPM, for 5 minutes. Aspirate and discard the top layer and transfer a sufficient quantity of the remaining bottom layer directly into an HPLC vial. Placebo Solution Prepare a single preparation in the same manner as a sample, using Placebo KORU 2 Cream in place of active formulation. |

*Note:
n-Heptane is used to remove oily excipient from the sample matrix only and as such does not contribute to the final volume of the Sample Working Solution. Actives are distributed on the bottom 5 mL layer of the biphasic mixture.

Gradient Elution Program

| Time (min) | Mobile phase A (% v/v) | Mobile phase B (% v/v) |
|---|---|---|
| 0 | 100 | 0 |
| 20 | 100 | 0 |
| 21 | 80 | 20 |
| 24 | 80 | 20 |
| 24.1 | 100 | 0 |
| 30 | 100 | 0 |

Example 9: Preparation of Lopinavir Only Ointment for Use According to the Invention For all formulations present below, all materials used are pharmaceutical grade (either US Pharmacopeia or European Pharmacopeia).
The manufacture of the composition containing lopinavir according to the invention is described below in reference to Table 6.
  i. Into a main mixing vessel add 1 and 3 and stir to dissolve
  ii. Into the main vessel add 4 and stir to dissolve
  iii. Into the main vessel add 2 and stir (low shear at 60 rpm and periodically homogenize at 600 rpm to dissolve) at −0.5 bar vacuum and ambient temperature to blend components until a very smooth consistency is achieved.
  iv. Discharge the product into well labelled polypail.
  v. Pack composition into aluminum tubes, suitable for dispensing composition.
  vi. The product can be stored at ambient conditions.

TABLE 6

| # | Ingredient | MP ° C. | Function(s) | % w/w | g/batch |
|---|---|---|---|---|---|
| 1 | Oleic acid | 13 | Unsaturated free fatty acid, Solvent, Permeation enhancer | 62.00 | 1240.0 |
| 2 | Stearic acid | 69 | Stiffening agent | 25.80 | 516.0 |
| 3 | Butylatedhydroxy-toluene | 70 | Antioxidant | 0.20 | 4.0 |
| 4 | Lopinavir** | 124 | API | 12.000 | 240.0 |
| | TOTAL | | | 100.000 | 2000.0 |

This particular composition was found to be a highly homogeneous system prepared using a simple mixing process without the need for high processing energy or heating and possess a high degree of manufacturing consistency and low variability.

It was also found that the formulation does not liquify at room temperature and is therefore surprisingly very well suited to being retained both topically and mucosally (even without the need for a mucoadhesive such as HPMC).

Upon application at a site of application of, components of the ointment vanish rapidly leaving minimal or no visible residue. Advantageously, the composition during and after application is silky an non-greasy. Furthermore, the high oleic acid level tends to give the composition a high penetration potential, improving API release and permeation at the site of application.

The viscosity of the composition was measured. The ointment was found to have an complex viscosity of about 4000 cps when measured at 25° C. and 0.5% strain at an angular frequency of 0.1 rad/s and about 400 cps when measured at 25° C. and 0.5% strain at an angular frequency of 1 rad/s.

The following methodology was used to determine the rheological response of the composition. A Discovery Hybrid Rheometer (Model HR-3, TA instruments) was used. The sample was introduced onto the peltier plate (base) in excess (1-2 g), and the spindle lowered to make contact with the sample. The excess sample was cleaned up. The spindle was then rotated in a predetermined fashion to exert a series of shear forces on the sample. The various sample shear force response parameters (complex viscosity, storage and loss moduli, tan δ) were captured and then plotted in order to make conclusions regarding inherent sample attributes.

Instrument parameters for the purpose of capturing complex viscosity, storage modus and loss modulus are as follows:—

Peltier temperature: 25° C.

Sample size: Approximately 1 g

Oscillation frequency method parameters:

Speed range 0.1 to 1 rad/s

Strain 0.5%

Spindle 40 mm parallel plate

Gap setting 1000 µm

An organoleptic assessment was also conducted:
Dosing Procedure
1 Remove the cap from the tube
2 Dispense a small amount of the ointment onto a clean fingertip.
3 With the fingertip, apply the ointment to the affected skin area, rubbing gently.
4 Replace the cap on the tube
Observations: The opaque ointment presents as easy to dispense from the tube, and is controllable on the skin during rubbing. After a short period of rubbing, the ointment clarifies to leave the skin non-tacky and with minimal greasiness. Approximately 10 minutes after dosing, the skin presents as silky, with negligible greasiness. These attributes denote an ointment as suitable for topical application.

Example 10: Preparation of Lopinavir Only Lip Balm (Contained in a Lipstick-Style Tube) According to the Invention For the formulation presented below, all materials used are pharmaceutical grade (either US Pharmacopeia or European Pharmacopeia) except for white ceresin wax, which is Japanese Pharmaceutical Excipient grade.
The manufacture of the composition containing lopinavir according to the invention is described below in reference to Table 7.
  i. Into a main vessel add 1, 2, 3, 4, 5, 6.
  ii. Heat to melt and stir by hand until clear liquid is present. Processing time should be 60 minutes.
  iii. Discharge the product into well labelled sealed jar to cool.
  iv. Product presents as a stiff ointment suitable to be used as a lip balm.

TABLE 7

| # | Ingredient | MP °C. | Function(s) | % w/w | g/batch |
|---|---|---|---|---|---|
| 1 | Oleic acid | 13 | Unsaturated free fatty acid, solvent, Permeation enhancer | 60.00 | 120.0 |
| 2 | Stearic acid | 69 | Stiffening agent | 15.00 | 30.0 |
| 3 | Ceresin wax | 65 | Thickener | 15.00 | 30.0 |
| 4 | polyoxyl-100 stearate | 59 | Thickener | 5.00 | 10.0 |
| 5 | Butylatedhydroxy-anisole | N/A | Antioxidant | 0.20 | 0.4 |
| 6 | Lopinavir | 124 | API | 5.000 | 10.0 |
| | TOTAL | | | 100.200 | 200.4 |

The viscosity of the composition was measured. The lip-balm was found to have an complex viscosity of about 1666 cps when measured at 37° C. and 0.5% strain at an angular frequency of 0.1 rad/s through to about 281 cps when measured at 37° C. and 0.5% strain at an angular frequency of 1 rad/s.

Example 11: Preparation of Lopinavir Only Anhydrous Oil in Polyol Emulsion According to the Invention For the formulation presented below, all materials used are pharmaceutical grade (either US Pharmacopeia or European Pharmacopeia).

The manufacture of the composition containing lopinavir according to the invention is described below in reference to Table 8.
  i. Into main vessel dissolve 4 into 1.
  ii. Add 2 and 3 into main vessel.
  iii. Homogenize to thicken.

TABLE 8

| # | Ingredient | Function(s) | % w/w | g/batch |
|---|---|---|---|---|
| 1 | Oleic acid | oil phase | 50.00 | 150.0 |
| 2 | glycerol | polyol phase | 30.00 | 90.0 |
| 3 | polysorbate 20 | surfactant | 15.00 | 45.0 |
| 4 | Lopinavir | API | 5.000 | 15.0 |
| | TOTAL | | 100.000 | 300.0 |

The composition uses two distinct non aqueous phases together. System stability to avoid separation into two phases would require the levels of the components to be optimized to yield a stable critical micelle event (emulsion).
Case Studies:

Example 12

A male subject aged 45 with a history of developing recurrent oral lesions (cold sores) every 2-4 months presented with symptoms of a visible lesion in August 2018. The formulation of Example 7 Table 1 was administered to the lesion 3-4 times daily for a period of 4 days. The outcome was resolution of the lesion (blister) within 4 days, with a further 4 days to fully heal to normal (no signs of redness or inflammation).
A lesion in the same location of the lip reoccurred within 4 weeks and was treated again with the same formulation 3-4 times per day for 4 days. Again the outcome was resolution of the lesion within 4 days. The subject was surprised to note that the lesion was significantly less aggressive during this repeat occurrence, and return to normal was several days faster.
Most significantly no recurrence of lesions occurred during a follow up period of 19 months following the two treatments (current date early May 2020). This non-reoccurrence was surprising and unusual given a) the timeframe and b) the absence of lesions during the New Zealand summer period when the subject's lesions are typically triggered during this time of year (due to higher ultra violet light exposure).
These results demonstrate that compositions according to the invention are particularly effective for treating and preventing the recurrence of HSV-related conditions such as cold sores.

Example 13

A female aged 60 with history of developing recurrent oral lesions whenever she gets a head cold presented with skin cracking of the upper lip, an early sign for her of a cold sore. She applied the Lopinavir only formulation of Example 8 Table 5 to the lesion 4 times a day and found that the cream held the cold sore in its early stage, i.e., it didn't progress to the blister stage but dried up. Five days later she had a slightly noticeable lesion but much less puffed up and spread out than normally encountered.

Example 14

A male aged 48 with a history of developing oral cold sore present with symptoms of a visible lesion. He administered the formulation of Example 7 Table 1 three to four times daily for a period of 2 days. Over this time the lesion completely resolved.

Example 15

A female aged 46 with a history of developing recurrent oral lesions presented with a well advanced cold sore which had blistered. She applied the cream of Example 7 Table 1, three to four times daily for a period of 4 days by which time the cold sore had resolved.

Example 16

Figure 6:
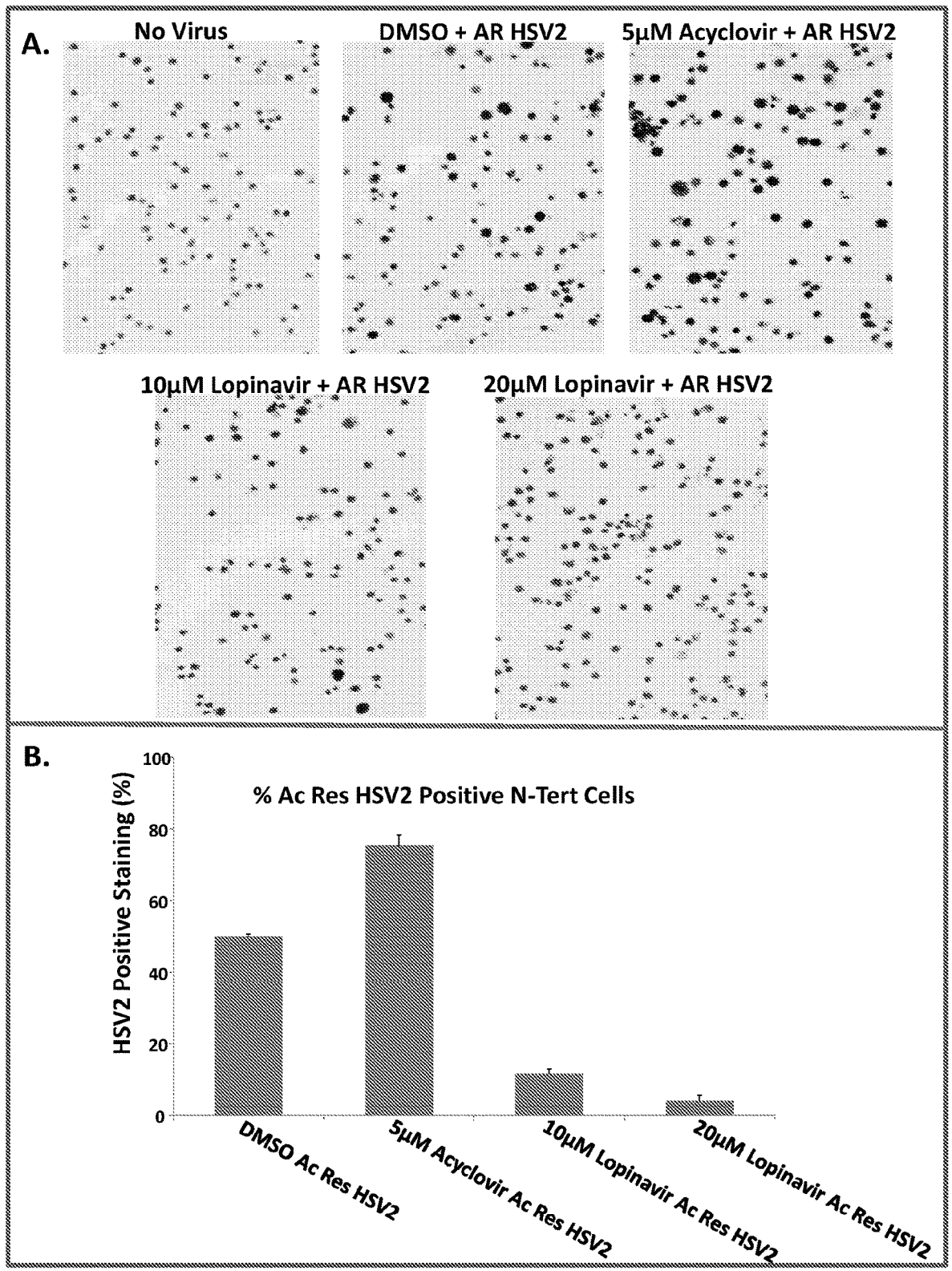
FIG. 6.
Figure 7:
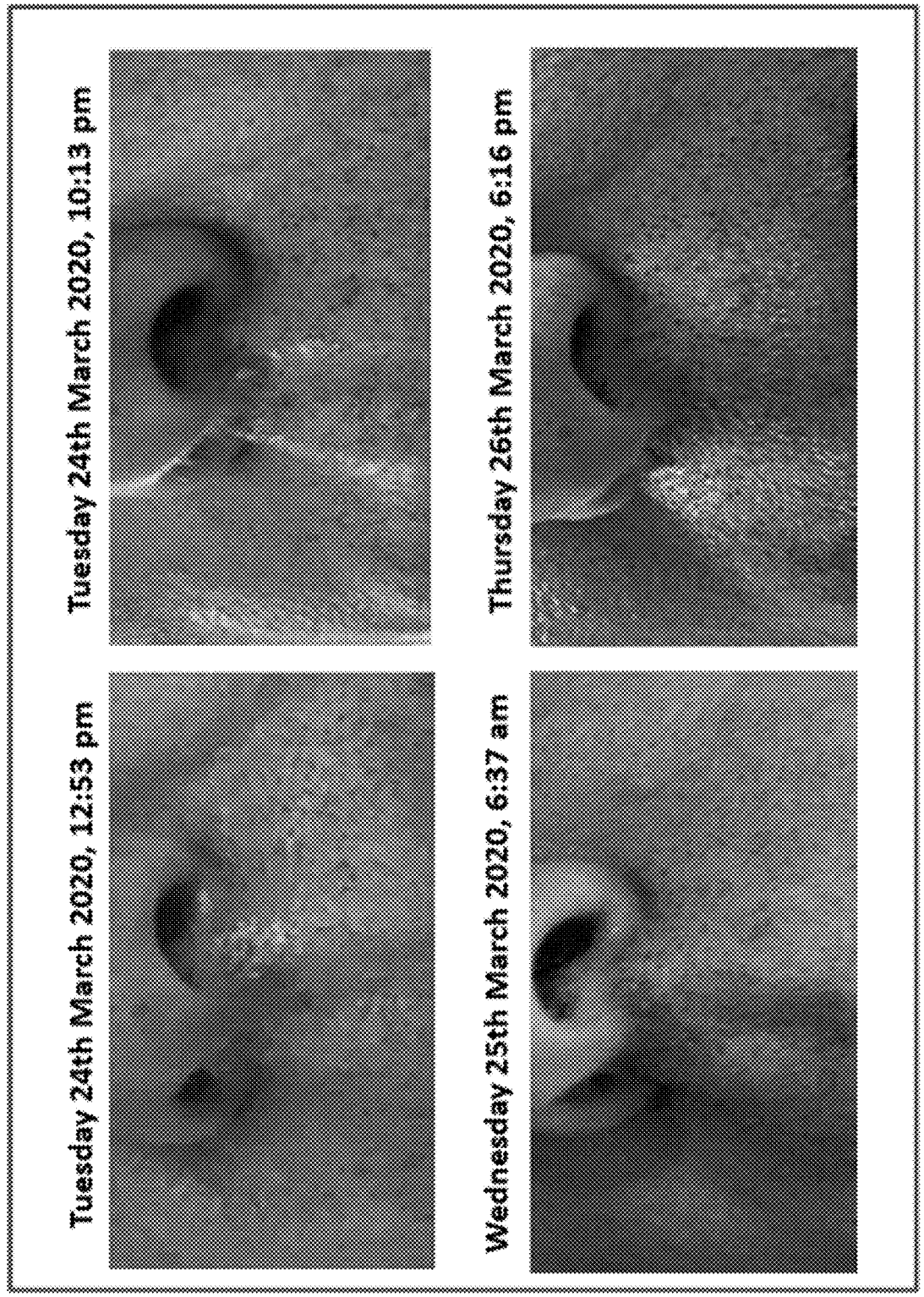
FIG. 7: shows images of an oro-labial HSV lesion treated with 12% w/w lopinavir ointment over a period of two days.

FIG. 6 shows images of a male aged 49 yrs with a lifelong history of oro-labial cold sores who was treated with the Lopinavir only ointment according to Example 9, Table 6 which contains lopinavir as single agent at 12% w/w. This was applied topically 3 times daily for 2 days starting on the 24$^{th}$ March at 12.53 pm (upper left photograph) and the last dose was applied on the 25$^{th}$ March at 10.00 pm. Remarkably, it can be seen that the lesion shows substantial resolution within 9 hours of commencing treatment (upper right photograph) and the final photo (lower right photograph, taken on the 26$^{th}$ March at 6.16 pm, shows this had completely resolved after 2 days.

The invention claimed is:

1. A method of treating and/or inhibiting the development or progression of conditions caused by, or associated with, Herpes Simplex Virus (HSV) in a subject in need of such treatment or inhibition comprising administering a therapeutically effective amount of a pharmaceutical composition comprising lopinavir to said subject,
wherein the lopinavir is present at a level of about 8 to 20% by weight of the total weight of the pharmaceutical composition.

2. The method according to claim 1 wherein the conditions are cutaneous or mucocutaneous HSV associated lesions comprising a cold sore, whitlow, genital or anal herpes.

3. The method according to claim 1 wherein the condition is caused by, or associated with, acyclovir resistant Herpes Simplex Virus.

4. The method according to any claim 1 wherein a sufficient amount of the pharmaceutical composition is given to the subject to prevent or reduce the reoccurrence of the condition caused by, or associated with, Herpes Simplex Virus.

5. The method according to claim 1, wherein lopinavir is the sole Active Pharmaceutical Ingredient in the pharmaceutical composition.

6. The method according to claim 1, wherein the pharmaceutical composition further comprises ritonavir.

7. The method according to claim 6 wherein lopinavir and ritonavir are included in the pharmaceutical composition in a weight ratio of about 12:1.

8. The method according to claim 1, wherein lopinavir in the pharmaceutical composition is present in a dose that is effective for treating HSV infection with or without attendant abnormal pathology.

9. The method according to claim 1 wherein the pharmaceutical composition is formulated for topical application.

10. The method according to claim 9 wherein the pharmaceutical composition is formulated for topical application to oral labia, nasal cavity, skin, peri-anal area or genitals of a subject.

11. The method according to claim 1 wherein the pharmaceutical composition is an ointment and comprises:
an unsaturated free fatty acid;
a stiffening agent; and
lopinavir alone, or lopinavir and ritonavir in a molar ratio of between 9:1 and 18:1;
wherein the unsaturated free fatty acid is present at a level of at least 20% by weight of the total pharmaceutical composition weight and wherein the pharmaceutical composition is a solid or semi-solid at room temperature.

12. The method according to claim 1 wherein the pharmaceutical composition is a cream.

13. The method according to claim 1 wherein the pharmaceutical composition comprises:
a. lopinavir as the sole Active Pharmaceutical Ingredient;
b. an unsaturated free fatty acid
c. a stiffening agent; and
d. optionally, additional excipients;
wherein the unsaturated free fatty acid is present at a level of at least 50% by weight of the total pharmaceutical composition weight; and wherein the pharmaceutical composition is a solid or semi-solid at room temperature; and wherein the pharmaceutical composition is an anhydrous composition selected from a non-aqueous emulsion, an ointment, a paste, a gel or a rigid dosage form such as pellets, solid or semi-solid stick compositions and lip-balms.

14. The method according to claim 13 wherein the pharmaceutical composition comprises:
a. lopinavir as the sole Active Pharmaceutical Ingredient;
b. an unsaturated free fatty acid;
c. a stiffening agent; and
d. optionally additional excipients;
wherein the unsaturated free fatty acid is present at a level of at least 50% by weight of the total pharmaceutical composition weight and wherein the pharmaceutical composition is a semi-solid at room temperature.

15. The method according to claim 14 wherein the unsaturated free fatty acid is oleic acid and the stiffening agent is stearic acid.

16. The method according to claim 14 wherein the unsaturated free fatty acid is present at a level of at least 60% by weight of the total pharmaceutical composition and the stiffening agent is present at a level of at least 20% by weight of the total pharmaceutical composition.

17. The method according to claim 1 wherein the pharmaceutical composition does not contain a muco-adhesive, a thickener or a blending aid.

18. The method according to claim 1 wherein the pharmaceutical composition is an ointment composition comprising:
a. about 9 to 15% by weight of lopinavir as the sole Active Pharmaceutical Ingredient;
b. about 55% to 70% by weight of oleic acid;
c. about 20% to 30% by weight of stearic acid; and
d. about 0.05 to about 0.5% of an antioxidant;
wherein all % are by weight based upon the total weight of the composition; and wherein the pharmaceutical composition is a semi-solid at room temperature.

19. The method according to claim 1, wherein the lopinavir is present at a level of about 12% by weight of the total weight of the pharmaceutical composition.

* * * * *